US012738012B2

(12) United States Patent
Madhavji

(10) Patent No.: US 12,738,012 B2
(45) Date of Patent: Sep. 15, 2026

(54) METHOD AND SYSTEM FOR ASSIGNING ANALYSIS OF REGIONS OF INTEREST IN AN IMAGE SET

(71) Applicant: Milan Madhavji, Mississauga (CA)

(72) Inventor: Milan Madhavji, Mississauga (CA)

( * ) Notice: Subject to any disclaimer, the term of this patent is extended or adjusted under 35 U.S.C. 154(b) by 0 days.

(21) Appl. No.: 19/531,008

(22) Filed: Feb. 5, 2026

(65) Prior Publication Data

US 2026/0170789 A1 Jun. 18, 2026

Related U.S. Application Data

(63) Continuation of application No. PCT/CA2024/051044, filed on Aug. 8, 2024.

(Continued)

(51) Int. Cl.
*G06V 10/25* (2022.01)
*G06T 7/00* (2017.01)

(Continued)

(52) U.S. Cl.
CPC ............ *G06V 10/25* (2022.01); *G06T 7/0012* (2013.01); *G06V 10/26* (2022.01); *G06V 20/70* (2022.01);

(Continued)

(58) Field of Classification Search
CPC ........ G06V 10/25; G06V 10/26; G06V 20/70; G06V 2201/03; G06T 7/0012;

(Continued)

(56) References Cited

U.S. PATENT DOCUMENTS 7,245,780 B2 7/2007 Attia et al.
7,657,070 B2 2/2010 Lefebvre (Continued)

OTHER PUBLICATIONS

"Cloud-Based Document Rights Management: Annotations: Fileopen." Cloud-Based Document Rights Management | Annotations | FileOpen, Feb. 26, 2021, web.archive.org/web/20210226093205/https://www.fileopen.com/annotations. (Year: 2021).*

(Continued)

*Primary Examiner* — Gregory A Morse
*Assistant Examiner* — Stefano Anthony Dardano
(74) *Attorney, Agent, or Firm* — Ziegler IP Law Group, LLC.

(57) ABSTRACT

A system includes an image set including at least one image. An assignment module is configured to assign a diagnosis region within the image set to a first diagnostician for analysis, to define a region of interest within the diagnosis region and to assign the region of interest to a second diagnostician for analysis. An annotation module is configured to define, via the first diagnostician, at least one first diagnostician annotation within the region of interest, the at least one first diagnostician annotation being assigned to the second diagnostician for review along with the region of interest and to define, via the second diagnostician, at least one second diagnostician annotation within the region of interest. A reporting module is configured to report the analyzed region of interest having the at least one second diagnostician annotation to the first diagnostician.

20 Claims, 15 Drawing Sheets

Related U.S. Application Data

(60) Provisional application No. 63/578,238, filed on Aug. 23, 2023.

(51) Int. Cl.
*G06V 10/26* (2022.01)
*G06V 20/70* (2022.01)
*G16H 30/40* (2018.01)

(52) U.S. Cl.
CPC ......... *G16H 30/40* (2018.01); *G06T 2200/04* (2013.01); *G06T 2207/10116* (2013.01); *G06T 2207/20104* (2013.01); *G06T 2207/30036* (2013.01); *G06V 2201/03* (2022.01)

(58) Field of Classification Search
CPC ....... G06T 2200/04; G06T 2207/10116; G06T 2207/20104; G06T 2207/30036; G16H 30/40; G16H 80/00; G16H 40/67; G16H 15/00; A61B 6/469; A61B 6/51
See application file for complete search history.

(56) References Cited

U.S. PATENT DOCUMENTS 8,150,110 B2 4/2012 Huo et al.
8,391,576 B2 3/2013 Kitamura et al.
8,831,182 B2 9/2014 Nelson
8,886,726 B2 11/2014 Venon et al.
8,953,858 B2 2/2015 Becker et al.
10,896,762 B2 1/2021 Abedin et al.
11,922,668 B2 3/2024 Ackermann et al.
2012/0308101 A1* 12/2012 Zeng ........................ G06T 12/30 382/131
2015/0205917 A1 7/2015 Mabotuwana et al.
2016/0253456 A1 9/2016 Goede et al.
2018/0046758 A1* 2/2018 Gogin ................. G06F 21/6254
2018/0060512 A1 3/2018 Sorenson et al.
2019/0096060 A1* 3/2019 Zhang ................... G06T 7/0014
2020/0126657 A1 4/2020 Chakrabarti et al.
2021/0233646 A1* 7/2021 Le Naour ............ G06Q 10/103
2022/0130128 A1 4/2022 Madhavji
2023/0021332 A1 1/2023 Vaillant et al.
2023/0197251 A1* 6/2023 Gurson .................. G16H 30/40 705/2
2023/0282011 A1* 9/2023 Teichmann ............ G06V 10/26 382/128
2024/0177836 A1* 5/2024 Paik ........................ A61B 5/742
2024/0369351 A1* 11/2024 Wang ................... G01B 11/022

OTHER PUBLICATIONS

Aljabri, M. et al. "Towards a better understanding of annotation tools for medical imaging: a survey" Multimed Tools Appl., vol. 81, pp. 25877-25911, Mar. 25, 2022 (Mar. 25, 2022), retrieved from https://link.springer.com/article/10.1007/s11042-022-12100-1 on Nov. 16, 2024 (Nov. 16, 2024).

* cited by examiner

METHOD AND SYSTEM FOR ASSIGNING ANALYSIS OF REGIONS OF INTEREST IN AN IMAGE SET

The present invention relates to a method and system for assigning the analysis of subsections or sub-volumes of images. More particularly, the present invention relates to a method and system for delineating, assigning and managing the responsibility for professional liability for regions of interest in radiographic images.

BACKGROUND

Medical imaging includes various techniques used to create visual representations of parts of the body which may not be visible from the outside of the body for the purposes of clinical analysis or diagnosis. Radiography is one such technique wherein X-rays are passed through one or more structures of the body. As the X-rays pass through the structures of the body, they are absorbed in varying amounts by different tissues. The X-rays which are not absorbed are detected by X-ray detectors and the X-ray signals produced by the detectors in response to the X-rays received by the detectors are used to generate radiographic images representing the structures of the body through which the X-rays passed.

Radiographic images may be provided as singular two-dimensional images or as an image series which includes a series of two-dimensional (2D) cross-sectional images (often called "slices") acquired as the scanner scans the patient.

Radiographic images require interpretation for diagnosis. Historically, the entire image (in the case of a singular image) or image series included in a patient study would be provided to a diagnostician and the diagnostician would be assigned the responsibility of reviewing and interpreting the information available in the entire image or image series. The diagnostician would be liable for interpreting all of the information available in the entire image or entire image series. Typically, the diagnostician produces a report of findings related to the images for which they are responsible.

An example of this would be the assignment of the responsibility for diagnosing a computed tomography (CT) scan to a radiologist. The radiologist would assess the entire image series and produce a report of findings. This may include incidental findings that are outside of the primary region of interest for the scan, but since the radiologist is responsible for the entire set of images in the CT scan, it is necessary to evaluate the image series in its entirety.

With the advent of artificial intelligence and computer vision, many diagnostic tasks that were once solely performed for diagnosticians are now being passed through an automated diagnostic system prior to being assessed by the diagnostician. Indeed, in some cases, the automated system produces the final diagnostic result, and human diagnosticians are not involved at all.

With the introduction of automation into the diagnostic workflow, there is often a situation where the automation flags a diagnostic issue with a low level of certainty. In these cases, the automation often alerts users that a finding has been potentially discovered that is outside of the capabilities of the automation and would therefore require assessment by a human. In this case, the acquirer of the image has a choice to diagnose it themselves if the acquirer has adequate diagnostic skill, expertise or knowledge. Alternatively, the acquirer of the image may send the entire image series to a third-party diagnostician for further analysis and diagnosis. Generally, this entails transfer of the image series to a different system from the system that produced the automated analysis. Upon the eventual receipt of the diagnostic result from the third-party diagnostician, the acquirer must then synthesize data from the automated system and from the third-party diagnostician to obtain a final diagnostic outcome for the image series.

Typically, the requirement to send an image series to a third-party diagnostic service for additional interpretation incurs a large overhead. The third-party diagnostic service is also responsible and liable for interpreting the image series. Accordingly, there is a necessity to fully duplicate the diagnostic work produced by the automation. Specifically, the third-party diagnostic service is responsible and liable for the entire image series and must therefore assess the entire image series, regardless of whether the automation already identified and diagnosed these areas to the satisfaction of the user that acquired the images.

As time goes on, the inclusion of automated diagnosis into the radiographic pipeline is likely to become the norm, and therefore, a more efficient method of obtaining third-party diagnostic expertise is necessary.

SUMMARY

The present invention relates to a method and system for assigning the analysis of subsections or sub-volumes of images. More particularly, the present invention relates to a method and system for delineating, assigning and managing the responsibility for professional liability for regions of interest in radiographic images.

In one aspect, there is provided a method having the steps of acquiring an image set including at least one image, assigning a diagnosis region within the image set to a first diagnostician for analysis, defining a region of interest within the diagnosis region, defining, via the first diagnostician, at least one first diagnostician annotation within the region of interest, assigning the region of interest and the at least one first diagnostician annotation to a second diagnostician for analysis, defining, via the second diagnostician, at least one second diagnostician annotation within the region of interest, and, reporting the analyzed region of interest having the at least one second diagnostician annotation to the first diagnostician. The image set may include a three-dimensional volumetric image. Defining the region of interest of the image set to be reviewed may include the step of outlining, within a bounding box, a three-dimensional region of the volumetric image having the region of interest therein.

In one aspect, the region of interest is a component of a collaborative digital infrastructure accessible by both the first diagnostician and the second diagnostician and assigning the region of interest to the second diagnostician for review is done within the collaborative digital infrastructure.

In one aspect, the method further includes the steps of determining whether further analysis is required, and if further analysis is required, then, defining at least one additional first diagnostician annotation within the region of interest, assigning the region of interest with the at least one additional first diagnostician annotation to the second diagnostician for review, and, defining, via the second diagnostician, at least one additional second diagnostician annotation within the region of interest.

In one aspect, the at least one first diagnostician annotation and the at least one second diagnostician annotation may be selected from a predetermined list of template annotations. The predetermined list of template annotations available for selection as second diagnostician annotations by the second diagnostician is dependent upon the first diagnostician annotation selected by the first diagnostician.

In one aspect, the method further includes the step of assigning a sub-region of the region of interest to at least one supplementary diagnostician for analysis. Assigning the sub-region may be by one of the first diagnostician and the second diagnostician. The method may further include the step of reporting the analyzed sub-region to at least one of the first diagnostician and the second diagnostician.

In another aspect, there is provided a system including an image set including at least one image, assignment module for assigning a diagnosis region within the image set to a first diagnostician for analysis, for defining a region of interest within the diagnosis region and for assigning the region of interest to a second diagnostician for analysis, an annotation module for defining, via the first diagnostician, at least one first diagnostician annotation within the region of interest, the at least one first diagnostician annotation being assigned to the second diagnostician for review along with the region of interest and for defining, via the second diagnostician, at least one second diagnostician annotation within the region of interest, and, a reporting module for reporting the analyzed region of interest having the at least one second diagnostician annotation to the first diagnostician. The image set may include a three-dimensional volumetric image. The system may further include a module configured to outline, within a bounding box, a three-dimensional region of the volumetric image having the region of interest of the image set to be reviewed therein.

In one aspect, the region of interest is a component of a collaborative digital infrastructure accessible by both the first diagnostician and the second diagnostician and assigning the region of interest to the second diagnostician for review is done within the collaborative digital infrastructure.

In one aspect, the first diagnostician determines whether further analysis is required. If further analysis is required, then the annotation module further defines at least one additional first diagnostician annotation within the region of interest, the assignment module assigns the region of interest with the at least one additional first diagnostician annotation to the second diagnostician for analysis, the second diagnostician defines at least one additional second diagnostician annotation within the region of interest and the reporting module reports the analyzed region of interest having the at least one additional second diagnostician annotation within the region of interest to the first diagnostician.

In one aspect, the at least one first diagnostician annotation and the at least one second diagnostician annotation is selected from a predetermined list of template annotations. The predetermined list of template annotations available for selection as second diagnostician annotations by the second diagnostician is dependent upon the first diagnostician annotation selected by the first diagnostician.

In one aspect, the assignment module is configured to assign a sub-region of the region of interest to at least one supplementary diagnostician. The reporting module may be configured to report the analyzed sub-region to at least one of the first diagnostician and the second diagnostician.

The present invention identifies the regions or subsections of any image or image series that is intended for any specific diagnostician to interpret. As a result, the responsibility and liability for the diagnosis of subsegments of an image set, image or image series can be clearly defined. Moreover, the responsibility and liability for the diagnosis of subsegments of an image or image series can be distributed amongst more than one potential diagnostician or diagnostic algorithm. By clearly identifying the person or algorithm that is responsible for interpreting any given subsection of an image, the ultimate responsibility for the liability associated with the diagnosis of that subsection of an image is also assigned to a specific individual or entity.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

The present invention relates to a method and system for assigning the analysis of subsections or sub-volumes of images. More particularly, the present invention relates to a method and system for delineating, assigning and managing the responsibility for professional liability for regions of interest in radiographic images.

Figure 1:
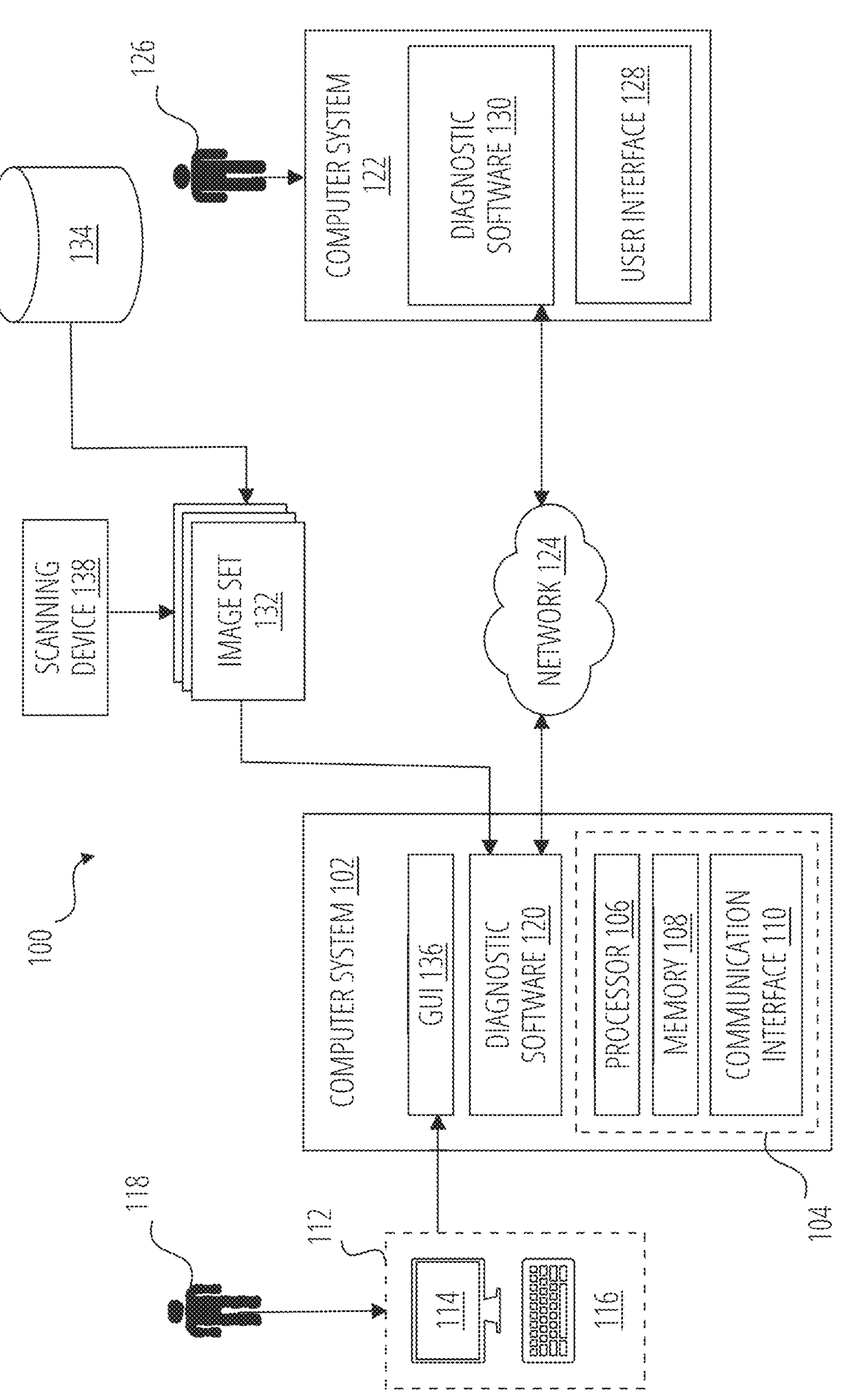
FIG. 1 illustrates a system according to one aspect.

FIG. 1 illustrates a system 100 having an electronic annotation system in accordance with one aspect of the present disclosure.

System 100 includes a first computer system 102 having a controller 104 including at least one first processor 106, a first memory 108 configured to store one or more first program instructions and at least one communication interface 110. The first computer system 102 is preferably connected to at least one first user interface 112 which may include at least one first display device 114 and at least one first user input device 116. First display device 114 may include, for example, a computer monitor. The at least one first display device 114 may be employed to present data from system 100 including, but not limited to text data, image data, performance data, alerts or the like. The first user input device 116 receives inputs from a user, such as first diagnostician 118. First display device 114 and first user input device 116 are preferably coupled in data exchange communication with first computer system 102 by way of a suitable transmission medium that may include wired or wireless portions. The at least one first display device 114 and the at least one first user input device 116 are shown in FIG. 1 as being bundled together in first user interface 112. In another aspect, first display device 114 and first user input device 116 may be standalone components of system 100.

The first processor 106 may include any one or more processing elements, micro-controllers, circuitry, field programmable gate array (FPGA) or other processing system, and resident or external memory for storing data, executable code, and other information accessed or generated by first computer system 102. Therefore, first processor 106 may include any microprocessor device configured to execute algorithms or program instructions. In general, the term "processor", may be broadly defined to encompass any device having one or more processing elements which execute a set of program instructions from one or more processing elements or any device having one or more processing elements which execute a set of program instructions from a non-transitory memory medium, wherein the set of program instructions is configured to cause the one or more processors to carry out any of the one or more process steps.

The first memory 108 may include any storage medium known in the art suitable for storing the set of program instructions executable by the associated one or more processors. For example, first memory 108 may include a non-transitory memory medium. For instance, first memory 108 may include but is not limited to, a read-only memory (ROM), a random access memory (RAM), a magnetic or optical memory device (e.g., disk), a magnetic tape, a solid state drive, flash memory (e.g., a secure digital (SD) memory card, a mini-SD memory card, and/or a micro-SD memory card), universal serial bus (USB) memory devices, and the like. The first memory 108 may be configured to provide display information to the first display device 114. In addition, first memory 108 may be configured to store user input information first user input device 116 of first user interface 112. First memory 108 may be housed in a common controller housing with the one or more first processors 106. First memory 108 may alternatively or in addition, be located remotely with respect to the spatial location of the processors and/or the controller 104 may access a remote memory (e.g., server), accessible through a network (e.g., internet, intranet, and the like).

The controller 104 may be configured to perform one or more process steps, as defined by the one or more sets of program instructions. The one or more process steps may be performed iteratively, concurrently and/or sequentially. The one or more sets of program instructions may be configured to operate via a control algorithm, a neural network (e.g., with states represented as nodes and hidden nodes and transitioning between them until an output is reached via branch metrics), a kernel-based classification method, a Support Vector Machine (SVM) approach, canonical-correlation analysis (CCA), factor analysis, flexible discriminant analysis (FDA), principal component analysis (PCA), multidimensional scaling (MDS), principal component regression (PCR), projection pursuit, data mining, prediction-making, exploratory data analysis, supervised learning analysis, Boolean logic (e.g., resulting in an output of a complete truth or complete false value), fuzzy logic (e.g., resulting in an output of one or more partial truth values instead of a complete truth or complete false value), or the like. For example, in the case of a control algorithm, the one or more sets of program instructions may be configured to operate via proportional control, feedback control, feedforward control, integral control, proportional-derivative (PD) control, proportional-integral-derivative (PID) control, or the like.

The communication interface 110 may be operatively configured to communicate with one or more components of the first computer system 102 and/or controller 104. For example, communication interface 110 may also be coupled (e.g., physically, electronically, and/or communicatively) with the at least one first processor 106 to facilitate data transfer between components of the first computer system 102, other components of system 100 and first processor 106. For instance, the communication interface 110 may be configured to retrieve data from the at least one first processor 106, or other devices, transmit data for storage in the first memory 108, retrieve data from storage in the first memory 108, or the like. By way of another example, controller 104 may be configured to receive and/or acquire data or information from other systems or tools by a transmission medium that may include wireline and/or wireless portions. In yet another example, controller 104 may be configured to transmit data or information (e.g., the output of one or more procedures of the inventive aspects disclosed herein) to one or more systems or tools by a transmission medium that may include wireline and/or wireless portions (e.g., a transmitter, receiver, transceiver, physical connection interface or any combination thereof). In this regard, the transmission medium may serve as a data link between the controller 104 and the other components of first computer system 102 and system 100. In addition, controller 104 may be configured to send data to external systems via a transmission medium (e.g., network connection).

The first computer system 102 is operable by a first diagnostician 118 via first user interface 112. The first diagnostician 118 may be a human diagnostician, such as any person having authorized access to patient data or information, such as a healthcare practitioner or a patient. Preferably, first diagnostician 118 is a human professional. In another aspect, the first diagnostician 118 is a controller for an automated system such as one or more machine learning models, an "artificial intelligence" (AI) system and/or other automated diagnostician. An automated diagnostic system could include a machine learning or "artificial intelligence" engine trained to autonomously complete certain diagnostic tasks. In some instances, the automated diagnostic system may complete the initial diagnosis without the need for involvement of a human diagnostician.

Embedded within or accessible to the first computer system 102 is diagnostic software 120. Diagnostic software 120 may exist in various forms, such as being embedded on a hard drive of first computer system 102, stored on a server in data communication with first computer system 102 or is accessible as a third-party software that can be used as a service by first computer system 102. In another aspect, diagnostic software 120 may include one or more machine learning models or an "artificial intelligence" system capable of performing automated image analysis, accessible by first computer system 102. Diagnostic software 120 is configured to receive data inputs from first user interface 112 via graphical user interface 136. Such data inputs may include any health data or health-related data and may include stored historical data stored in data storage 134 or elsewhere that is accessible by diagnostic software 120 or data inputs entered by first diagnostician 118.

Diagnostic software 120 may output a complete diagnosis on its own based on the data inputs or may assist the first diagnostician 118 in making a diagnosis related to patient condition or treatment plans. The diagnosis may be output by diagnostic software 120 and may subsequently be used as inputs to one or more other components of system 100 for further processing or for triggering new actions. Through comprehensive data analysis, diagnostic software 120 is able to identify patterns, anomalies, or markers that may indicate the presence of or potential for developing a particular medical condition. Additionally, diagnostic software 120 aids in risk assessment, which is beneficial for preventive care and disease management. For specialized medical practitioners such as dental radiologists, diagnostic software 120 assists with interpretation of medical images by leveraging computerized image processing techniques. In this context, diagnostic software 120 can enhance the visibility of anatomical structures, improve image quality, and assists in the identification of abnormalities or lesions that may not be easily detectable in images analyzed only by the human eye. Use of diagnostic software 120 can lead to faster and more accurate diagnoses, facilitating timely intervention and improved patient outcomes.

An example of health data may include an image set 132, which includes at least one image acquired from a patient. Preferably, the at least one image is a radiographic image. Image set 132 may be stored in data storage 134. Image set 132 may be generated by conducting a new scanning operation to obtain new patient images, may be retrieved from data storage 134 or may be obtained from a patient study.

First computer system 102 is in data exchange communication with a second computer system 122 via network 124. Second computer system 122 is operable by a second diagnostician 126. The second diagnostician 126 may be a second healthcare practitioner or third-party service to whom review of patient image data may be referred. In this aspect, the second diagnostician 126 may interact with second computer system 122 via suitable user interface 128. This user interface 128 allows for communication and interaction between the second diagnostician 126 and the second computer system 122. The second computer system 122 has embedded thereon or has access to diagnostic software 130 which may be the same software as diagnostic software 120, accessible by both of the first diagnostician 118 and the second diagnostician 126 via a collaborative information technology infrastructure or may be another software that is compatible with diagnostic software 120 in communication with first computer system 102. Diagnostic software 130 of second computer system 114 may exist on a hard drive of second computer system 122, on a server in data communication with second computer system 122 or may be a third-party software accessible as a service by second computer system 122. Second diagnostician 126 operates second computer system 114 for performing a diagnosis on the image set assigned by the first diagnostician 118.

Diagnostic software 120 and diagnostic software 130 aid medical practitioners and healthcare service providers in the interpretation of medical images, particularly radiographic images (e.g., X-rays, CT scans, MRI scans). Diagnostic software 120 and 130 may leverage sophisticated algorithms, machine learning, and artificial intelligence techniques to analyze and process vast amounts of digital medical images. In the context of radiographic image analysis, diagnostic software 120 and 130 enable the detection, segmentation, and classification of various abnormalities and pathologies within an image set. Diagnostic software 120 and 130 can precisely identify anatomical structures, localize specific regions of interest, and highlight potential indications of diseases or injuries. Diagnostic software 120 and 130 may incorporate comprehensive libraries of image patterns, reference data, and established diagnostic criteria to assist in the interpretation and diagnostic decision-making process. Diagnostic software 120 and 130 serve as a tool for accurate and efficient diagnosis of medical images.

Diagnostic software 120 is configured to provide the first diagnostician 118 with the ability to insert annotations into images of image set 132. The annotation feature within diagnostic software 120 allows the first diagnostician 118 to mark regions of interest directly on the medical image either for future reference by first diagnostician 118 or for the benefit of other practitioners involved in patient care. These annotations help to draw attention to specific anatomical structures, abnormalities, or regions requiring further analysis or examination. Diagnostic software 120 is further configured to create an assignable task out of a region of interest containing one or more annotations. The assignable task may be assigned to second diagnostician 126, for example. Second computer system 122 is notified that the assignable task has been assigned to them and they may then review the region of interest identified in the assignable task and work to complete the task.

Once the task has been completed by second diagnostician 126, the task is marked as complete and notification is sent to the first diagnostician 118 who created the task along with the remarks and notes entered by second diagnostician 126. The first diagnostician 118 may then review remarks entered by the second diagnostician 126. The first diagnostician 118 has the option to close the task or re-assign the task to the second diagnostician 126 with additional instructions.

The annotation function coupled with the assignment function allows for effective communication and collaboration of healthcare professionals by providing a means to highlight, describe and collaborate upon specific areas or findings within the medical images. The annotation and assignment functions allow for a volume of patient image data to operate as a collaborative workspace. By indicating key regions of interest within one or more images of an image set 132, the annotations provide visual references for others, such as a second diagnostician 126, who may need to review the same images. By using the assignment module 202 to assign only the specific regions of interest or findings to the second diagnostician 126, the second diagnostician 126 is limited only to reviewing those regions of interest and does not unnecessarily spend additional time reviewing other areas of the image that do not require review or assessment. This reduces turnaround time for patient care by reducing duplication of work with first diagnostician 118 and associated cost since the second diagnostician 126 is prevented from reviewing all images provided to them in their entirety from start to finish. By limiting the questions, remarks or notes available to the first diagnostician 118 and the second diagnostician 126, communication between the two parties is clear and leaves little room for miscommunication or error. Where the annotation is unclear in its visual representation or its meaning, such as by way of misspelling, the second diagnostician 126 must contact the first diagnostician 118 for further clarification. This introduces confusion and delay into the workflow, thereby reducing the turnaround time and reducing potential improvements in patient care. The ability to insert annotations into medical images, assign them to other practitioners and to do so in a way which leaves little room for misinterpretation and miscommunication through diagnostic software greatly enhances the collaboration and communication among healthcare providers. It facilitates the transfer of knowledge, allows for second opinions, and helps maintain a comprehensive record of visual findings, ultimately leading to more effective decision-making and improved patient care.

Figure 2:
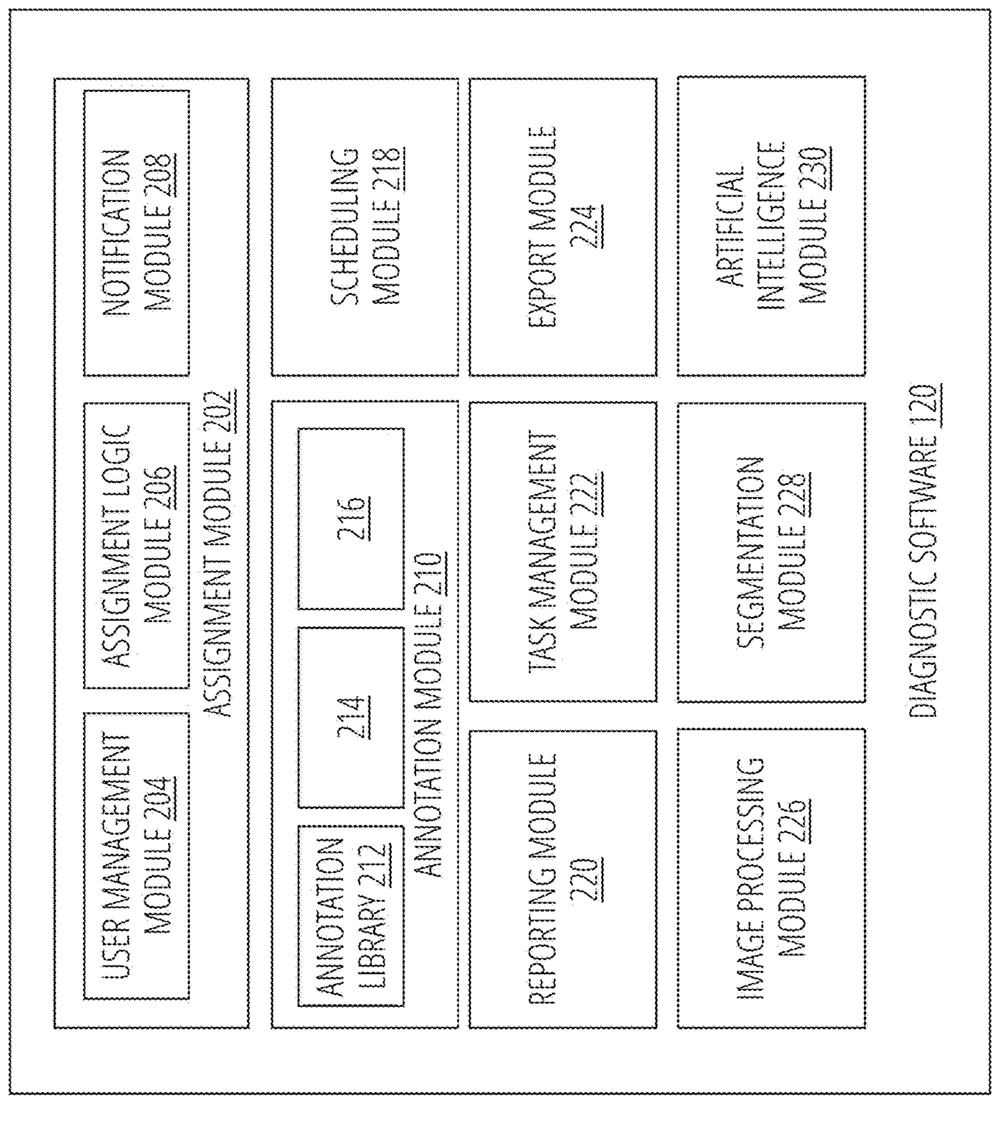
FIG. 2 illustrates diagnosis software, according to one aspect.

FIG. 2 is a block diagram illustrating diagnostic software 120 and modules thereof for enabling and facilitating functions of system 100 according to aspects described herein. It should be understood that diagnostic software 120 and diagnostic software 130 are similar in function and, in some aspects, may be the same or similar software deployed for operability with different computers operated by the first diagnostician 118 or the second diagnostician 126, as the case may be and mutually accessible via a shared or collaborative information technology infrastructure, such as a shared cloud environment. Accordingly, aspects are described herein with respect to diagnostic software 120 but should be understood to apply equally or similarly to aspects of diagnostic software 130 and vice versa.

Diagnostic software 120 includes an assignment module 202 which allows for the creation and modification of at least one assignable task within the image set 132 and assignment or re-assignment of the at least one assignable task to a user. Creation and modification of a task may include setting task descriptions, associated deadlines, priorities, and any relevant details needed to complete the task, for example. Preferably, assignment module 202 is embedded within diagnostic software 120. However, assignment module 202 may be housed independently of diagnostic software 120 as a separate piece of software stored on the same or a different computer system or on a cloud system.

As is further described hereinafter, the first diagnostician 118 defines a diagnosis region (FIG. 4) within image set 132. "Diagnosis region" refers to the region of the image or image set that is targeted for diagnosis by the first diagnostician. Since the first diagnostician is typically the primary physician of the patient, the diagnosis region will typically include all image data provided to the first diagnostician or all image data provided relating to a specific body structure of the patient.

In one aspect, assignment module 202 creates a task for analysis of the diagnosis region and assigns it to the first diagnostician 118. Thereby, the analysis of the diagnosis region by first diagnostician 118 may be tracked.

As is further described hereinafter, first diagnostician 118 may also further define at least one region of interest within the diagnosis region for further analysis by second diagnostician 126.

In one aspect, assignment module 202 creates an assignable task for analysis of the at least one region of interest. This task may be assigned directly to second diagnostician 126 using diagnostic software 120 or may be first assigned to first diagnostician 118 to be subsequently assigned to second diagnostician 126. Thereby, analysis of the at least one region of interest may be tracked.

In one aspect, diagnostic software 120 further includes a user management module 204 which is embedded within or coupled in data exchange communication with assignment module 202. The user management module 204 facilitates the creation and maintenance of user profiles, including skills, education, qualifications, roles, permissions, and access controls. Assignment module 202 selects an appropriate user profile using the user management module 204 when assigning a task to a user.

In one aspect, diagnostic software 120 further includes an assignment logic module 206 which is embedded within or coupled in data exchange communication with assignment module 202. The assignment logic module 206 enables the manual or automatic assignment of tasks to specific users or groups based on certain rules or criteria such as workload balancing, skill matching, user roles and/or user permissions. For example, once the task is created, the assignment logic module may provide a list of suitable assignee users for the task. The list of suitable assignees may include information related to each of the potential assignees such as their areas of expertise or their years of experience. It should be understood that the list of suitable assignees for the task may include not only individuals but also groups of individuals or teams to which the task may be assigned. The user assigning the task, such as first diagnostician 118, may select an assignee from the list of suitable assignees or may rely on the assignment logic module to automatically assign the task to another user.

In one aspect, diagnostic software 120 further includes a notification module 208 which is embedded within or coupled in data exchange communication with assignment module 202. The notification module 208 notifies users when a task is assigned to them, when changes are made, or when task-related deadlines are approaching. Notification can be by any suitable means, such as email alerts, in-app notifications, or SMS. In one aspect, the notification includes a link that allows the recipient to open the task directly from the communication containing the notification, such as a hyperlink embedded in an email which, when clicked, directs the recipient to the task.

Diagnostic software 120 further includes an annotation module 210, which allows a user to annotate one or more images of the image set 132. Annotations may include any suitable marking, such as circles, arrows, or text boxes. Preferably, annotations include comments or remarks such as an identification of anatomical structures, identification of pathologies or other abnormalities, measurements, comparisons with previous images, notes related to implant planning, anomalies or developmental variations, notes or previous or future dental work, reference lines for surgical planning, textual notes or diagnostic codes or references, for example. These annotations facilitate effective communication among healthcare providers and play a significant role in ensuring high-quality patient care. Preferably, annotations are limited to one of the bounding box, the region of interest, or both.

In one aspect, diagnostic software 120 further includes an annotation library 212 which is embedded within or coupled in data exchange communication with the annotation module 210. The annotation library 212 is a predetermined list or tree of notes or questions which users collaborating over a region of interest may use to communicate relevant information to one another. For example, a first user such as the first diagnostician 118 may select predetermined first diagnostician annotation (FIG. 12), which may include a note or question, from the annotation library 212. Such a selection may be made, for example, using first diagnostician annotation selection module 214 of annotation module 210. The selected first diagnostician annotation is included among the annotations related to the region of interest to be relayed to the second user, such as second diagnostician 126. Second diagnostician 126 may, in turn, select a second diagnostician annotation from a predetermined list of second diagnostician annotations (FIG. 14) in reply to the first diagnostician annotation. The second diagnostician annotation may include notes or answers that is or are related to the initial first diagnostician annotation. This may be facilitated, for example, by second diagnostician annotation selection module 216 of annotation module 210. Thereby, there is provided a standardized system for relaying important information between users. This prevents miscommunication due to lack of clarity or user-generated errors in the initial question to be answered and any subsequent replies. Thereby, turnaround time is reduced and the patient can expect a clearer analysis.

In one aspect, diagnostic software 120 includes a scheduling module 218 which manages scheduling of tasks. Scheduling module 218 may integrate with user or team calendars to help users or managers visualize their deadlines and manage their time efficiently. In one aspect, scheduling module 218 supports scheduling meetings or other time-specific activities related to tasks.

In one aspect, diagnostic software 120 includes a reporting module 220 which provides an overview of task status, progress, and overall project health. This can help managers and team members quickly understand what tasks are in progress, pending, or completed. This may be accomplished, for example, by way of a dashboard that allows a user to visualize task progress and completion.

In another aspect, diagnostic software 120 includes a task management module 222 which facilitates management of workflow at the task level rather than the user level. Task management module 222 allows for tasks to be prioritized based on their urgency and/or business impact. Task management module 222 also facilitates resource management and allocation, ensuring that no users, teams or resources are over-allocated or under-allocated, avoiding bottlenecks and workflow inefficiencies. Thereby, task workload can be managed while ensuring that critical tasks are completed on a priority basis.

Diagnostic software 120 may include an export module 224 which allows for exportation of information, such as annotations, images or portions thereof in a suitable format, such as JPEG or PNG, for example. Extraction of such information from diagnostic software 120 may make it easier to prepare patient reports or to collaborate on items outside of the diagnostic software 120 environment.

Diagnostic software 120 may include an image processing module 226 which may be used for enhancing and analyzing the image set 132. For example, image processing module 226 may be used for enhancing images by adjusting contrast or brightness or for applying various filters to highlight certain features, to scale the image, to sharpen the image to enhance the edges or structures, to remove noise or improve image clarity. Image processing module 226 may also provide tools for rotation and alignment of selected elements within an image, for taking measurements of structures, angles, orientations, areas or volumes.

In one aspect, diagnostic software 120 further includes a segmentation module 228 which is embedded within or coupled in data exchange communication with image processing module 226. The segmentation module 228 utilizes advanced algorithms to automatically or semi-automatically distinguish and isolate different structures within images, such as teeth, bones, nerves, and soft tissues. By accurately segmenting these structures, the software provides dentists and oral surgeons with precise, detailed visualizations that aid in diagnosis, treatment planning, and surgical simulation. The segmentation module 228 may include a user-friendly interface that allows the user to refine and adjust the segmentation to accommodate individual anatomical variations, thereby enhancing the accuracy and effectiveness of dental treatments. Additionally, the integration of machine learning and artificial intelligence in segmentation can further improve the speed and accuracy of the segmentation process.

In one aspect, diagnostic software 120 further includes an artificial intelligence module 230. Preferably, artificial intelligence module 230 is embedded within diagnostic software 120 or is locally stored on the same computing device and accessible by diagnostic software 120. However, artificial intelligence module 230, may be housed independently of diagnostic software 120 as a separate piece of software stored on the same or a different computer system or on a cloud system. Artificial intelligence module 230 may use artificial intelligence or machine learning algorithms to automatically detect and highlight potential abnormalities and can diagnose those abnormalities. Artificial intelligence module 230 may be enabled to independently diagnose diseases, pathologies or other abnormalities that are identifiable within the image set 132. Preferably, artificial intelligence module 230 provides decision support to users such as the first diagnostician 118 or the second diagnostician 126. Thereby, artificial intelligence module 230 may be used as a tool which facilitates faster, more efficient and potentially more accurate diagnoses based on patient information identified within the image set 132.

Figure 3:
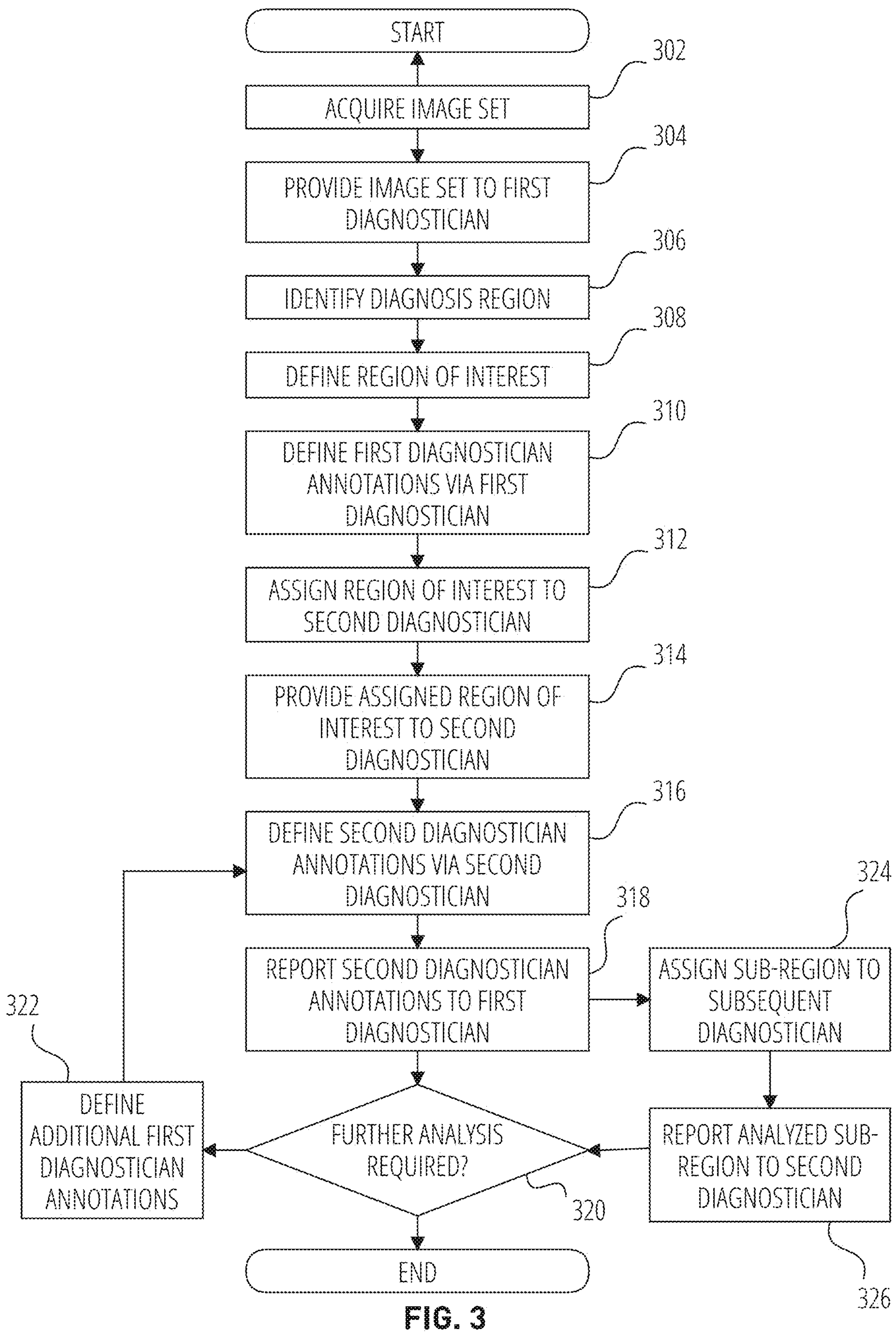
FIG. 3 illustrates a method, according to one aspect.

The method, according to one aspect, is shown in FIG. 3. In block 302, a scanning operation, such as a radiographic scanning operation, is performed on a person to be diagnosed, such as a patient. In one aspect, the image set 132 is of a body structure of a patient, such as an oral, dental or facial structure, for example. The scanning operation generates an image set 132 which includes at least one image. Preferably, image set 132 is a volumetric image including a three-dimensional representation of a body structure of the patient. However, it should be understood that in other aspects, image set 132 may include as few as a single two-dimensional image. The single image may be an optical image taken, for example, using an optical scanning device or may be a "slice" taken from a volumetric image.

In block 304, the image set 132 is provided to a first diagnostician 118. The image set 132 may be acquired by first diagnostician 118 from any suitable source, such as from a patient study or by the first diagnostician 118 conducting a fresh radiographic scan of a patient to obtain a new image set. An image set 132 may also be retrieved from archive or data storage 134.

In block 306, first diagnostician 118 identifies a diagnosis region within image set 132. "Diagnosis region" refers to the region of the image or image set that is targeted for diagnosis by the first diagnostician. Since the first diagnostician is typically the primary physician of the patient, the diagnosis region will typically include all image data provided to the first diagnostician or all image data provided relating to a specific body structure of the patient. As previously described, the first diagnostician 118 is responsible for reviewing and interpreting the information presented in the diagnosis region, image set 132, in this instance, for the purposes of diagnosing the information available therein.

In some instances, the first diagnostician 118 may identify a region of interest within the diagnostic region. The region of interest may be a region having an unusual pathology or in which an aberrant condition might be present. There may be instances where some aspect of the region of interest is outside of the realm of experience or skill or area of expertise of the first diagnostician 118. In such cases, the first diagnostician 118 may require input from another diagnostician, such as second diagnostician 126 in order to fully analyze the diagnosis region. In another aspect, the first diagnostician 118 may simply wish to solicit a second opinion from another practitioner.

In the case of an automated diagnostic workflow, situations may arise wherein the automated system identifies a diagnostic issue with a low level of certainty. In these cases, the automated system often alerts users, such as the first diagnostician 118, that a finding has been potentially discovered that is outside of the capabilities of the automated system and would therefore require assessment by a human. Accordingly, the automated system would identify the anomaly within a region of interest.

Preferably, the region of interest is defined by a bounding box surrounding the region of interest. A bounding box is typically a sphere, circle, rectangle or square outline that is drawn around the region of interest. In 3D volumetric images, the bounding box may take the form of a three-dimensional polygon of any number of sides, vertices and edges. Accordingly, the bounding box can surround a general region that contains the region of interest or may be custom fit to precisely surround the region of interest where it has a particular shape. The bounding box highlights or delineates the region of interest relative to other regions of the image. The bounding box may be added by the first diagnostician 118 or by an automated system using a suitable tool or utility within diagnostic software 120. Such a tool or utility might be included as a component of the assignment module 202, the annotation module 210 or the image processing module 226, for example. The bounding box is coupled in data exchange communication with the annotation module 210 so that annotations may be created, edited or removed in association with the data within the bounding box in accordance with one or more of the aspects described hereinafter.

In one preferred aspect, where diagnostic software 120 operates within a cloud-based system. Within this system, one of the bounding box, the region of interest or both, may be used to define a collaborative digital infrastructure. This infrastructure, accessible via a cloud service, enables users to store, share, and collaborate on the region of interest over a computer network. In this shared environment, the first diagnostician 118 or their information technology service provider can authorize access for another individual, such as the second diagnostician 126, to access the region of interest. Thereby, second diagnostician 126 gains permission to engage with the region of interest via the cloud service. Following the grant of access, first diagnostician 118 may assign tasks to second diagnostician 126 as further described hereinafter.

In one aspect, the first diagnostician 118 may refer the entire image set 132 to the second diagnostician 126 for further analysis and diagnosis. That is, the region of interest completely overlaps with the diagnosis region. Referral to second diagnostician 126 may entail transfer of the image set 132 to a third-party diagnostic service or to a different automated diagnostic system from the automated system that produced the automated analysis.

However, providing the entire image set 132, without limitation or boundary to the second diagnostician 126 transfers responsibility, risk and liability for the entire image set 132 to the second diagnostician 126. Therefore, it is advantageous to have a means by which the scope of the analysis by second diagnostician 126 is limited to the defined or predetermined region of interest or sub-volume of the image set 132 that is targeted by the first diagnostician 118 for further analysis by another diagnostician.

Figure 5:
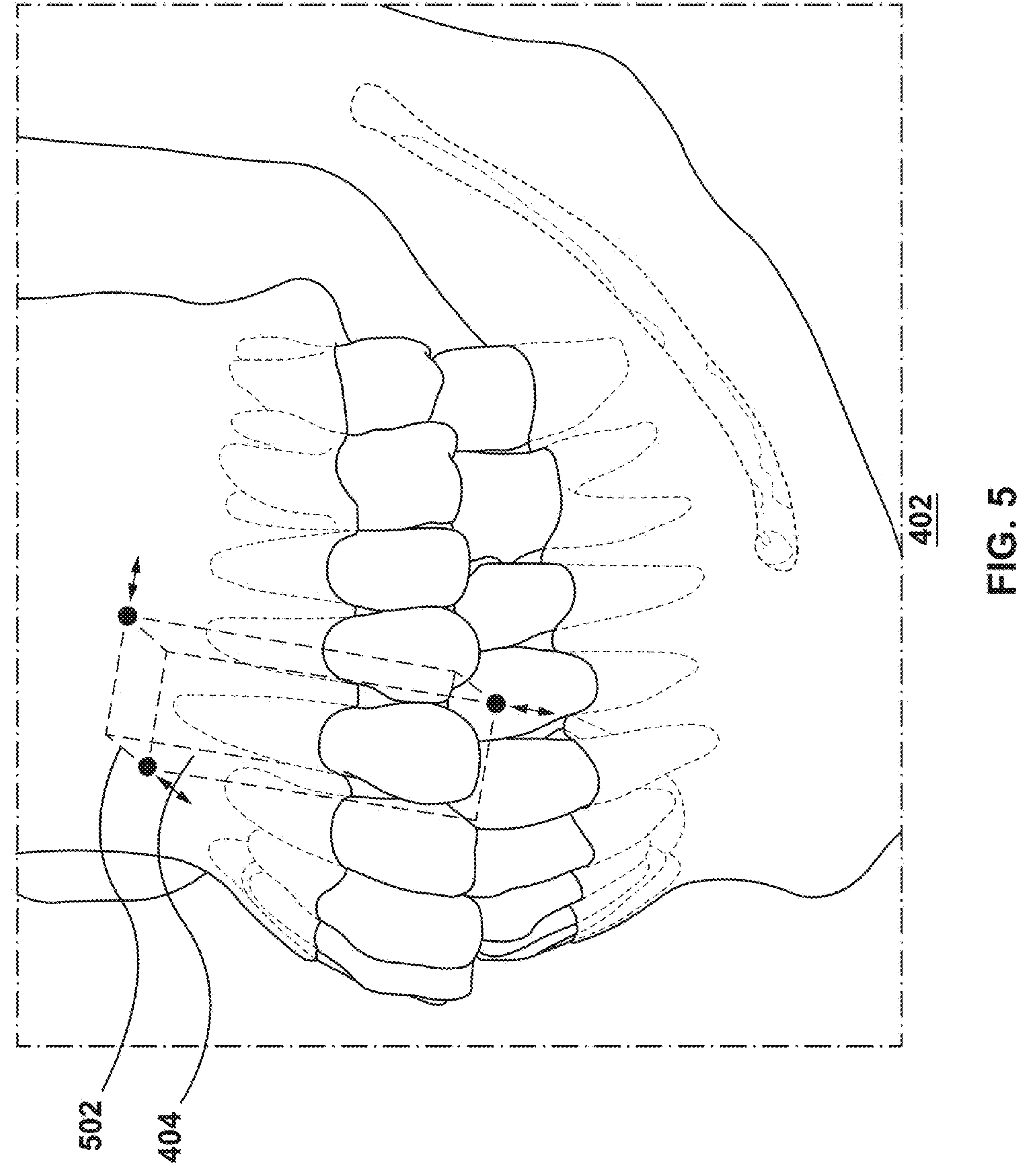
FIG. 5 illustrates a diagnosis region, according to one aspect.

In block 308, first diagnostician 118 defines a region of interest within the image set 132. "Region of interest" refers to the sub-region, subsection or sub-volume of the image set selected by the first diagnostician for assignment to the second diagnostician for further analysis, diagnosis, comment or feedback. Preferably, defining the region of interest of the image set 132 to be reviewed is done by outlining the region of interest using a bounding box (FIG. 5). The bounding box may be added by the first diagnostician 118, for example, using a suitable tool or utility of diagnostic software 120. This may be done manually by first diagnostician 118 or automatically via diagnostic software 120.

The region of interest may be further characterized by the presence of annotations input via a suitable annotation system, such as annotation module 210 of diagnostic software 120. Annotation module 210 allows the first diagnostician 118 to add notes, comments, feedback or questions related to the region of interest and directed to the second diagnostician 126. In one aspect, annotations may be applied to the region of interest in any suitable form, such as text, audio or image data. In one preferred aspect, annotations are selected from annotation library 212 that includes a list or conversation tree containing predetermined questions, comments or observations from which the first diagnostician 118 may select what is needed. The annotations are relayed to the second diagnostician 126 as part of the assigned region of interest. By providing annotations in such a format, miscommunication by way of errors in spelling, grammar, sentence structure is prevented. Thereby, the annotation information can be clearly communicated to the second diagnostician 126 in a predetermined, clear format, thereby preventing misunderstanding and misinterpretation on the part of the recipient.

It is preferred that annotations made within the region of interest are specific to the region of interest. Accordingly, annotations made within a region of interest may not be viewed from other areas of the image data, such as from other areas of the diagnostic region or from other regions of interest, should the image data include a plurality of regions of interest. Moreover, annotations made within a region of interest are preferably only visible to those responsible for interpreting data within the region of interest, such as, for example, the first diagnostician 118 and second diagnostician 126. As will be further discussed hereinafter, responsibility for the region of interest may be assigned to second diagnostician 126.

At block 310, first diagnostician 118 selects at least one first diagnostician annotation to be applied to the region of interest.

At block 312, the region of interest of the image is assigned via assignment module 202 to a reviewer, such as second diagnostician 126, for review.

At block 314, the assigned region of interest is provided to the second diagnostician 126 for review. The region of interest with annotations may be transmitted to the second diagnostician 126 by any suitable means, such as over network 124. The second diagnostician 126 may access the assigned region of interest and annotations using a compatible service, such as diagnostic software 130, having the capability to view the region of interest and the associated information. In one aspect, assignment module 202 may block, blur or obscure image data outside of the region of interest that has been assigned to the second diagnostician 126. In another aspect, the second diagnostician 126 may be granted "view only" permission for image data outside of the region of interest, thereby preventing addition of annotations to this area by second diagnostician 126. This provides an additional layer of protection against the second diagnostician 126 becoming responsible, legally or ethically, from having to review and provide comments on image information outside of the 202.

In one preferred aspect, one of the bounding box, the region of interest or both, may define a collaborative digital infrastructure. This infrastructure, accessible via a cloud service, enables users to store, share, and collaborate on the region of interest over a computer network. In this shared environment, the first diagnostician 118 or their information technology service provider can authorize access for another individual, such as the second diagnostician 126, to access the region of interest. Thereby, second diagnostician 126 gains permission to engage with the region of interest via the cloud service. Following the grant of access, first diagnostician 118 may assign tasks to second diagnostician 126 as further described hereinafter.

In block 316, the second diagnostician 126 provides at least one second diagnostician annotation and/or comments within the region of interest. As previously described diagnostic software 130 may include the same or similar features and functions to diagnostic software 120. Accordingly, diagnostic software 130 may include an annotation module 210 of its own that is compatible with that of diagnostic software 120 and therefore second diagnostician 126 may enter his or her own annotations to a region of interest, including notes, comments, feedback or questions. Annotations may be in any suitable form, such as text, audio or image data.

As with diagnostic software 120, annotation module 210 of diagnostic software 130 may include an annotation library 212 that includes a list of predetermined questions, comments or observations from which the second diagnostician 126 may select what is needed. The region of interest including the second diagnostician annotations is relayed back to the first diagnostician 118. Preferably, the annotation library 212 options available to the second diagnostician 126 is limited by the initial predetermined selections made by the first diagnostician 118. Thereby, the scope of responses available to the second diagnostician 126 is limited. By providing annotations in such a format, miscommunication by way of errors in spelling, grammar, sentence structure is prevented. Also, this provides further protection from liability and adopted responsibility for the second diagnostician 126 because commentary outside of the scope of the questions raised by the first diagnostician 118 is prevented. Thereby, the annotation information can be clearly communicated to the first diagnostician 118 in a predetermined, clear format, thereby preventing misunderstanding and misinterpretation on the part of the recipient.

At block 318, once the review by the second diagnostician 126 is completed and all of the second diagnostician 126 annotations have been entered and confirmed, the assignment module relays a report back to the first diagnostician 118. The review report may include any relevant information on the region of interest that has been added by the second diagnostician 126, including answers within the available scope permitted by the first diagnostician 118 and/or annotation module 210.

At block 320, a decision is made as to whether or not further analysis is required. This may be for any suitable purpose, such as if the second diagnostician 126 requires further information or clarification in order to complete his or her diagnosis or if the second diagnostician 126 has further questions or considerations to raise.

If further analysis is required, the method proceeds to block 322 wherein additional first diagnostician annotations are defined. The method then returns to block 316 for input of additional second diagnostician annotations. This process may repeat as many times as is needed until the first diagnostician 118 is satisfied with the analysis and has discharged his or her duties relating to analysis of the information provided in the image set.

If no further analysis is required, the method ends as the second diagnostician annotations have been reported to the first diagnostician at block 318.

In another aspect, second diagnostician 126 may assign a sub-region of the region of interest to one or more subsequent diagnosticians for analysis. This may occur where a finding in the sub-region is beyond the skill or scope of expertise of the second diagnostician 126, for example. In such a case, the subsequent diagnostician will review and analyze the sub-region. The reporting module may then report the analyzed sub-region to the second diagnostician 126 or directly to the first diagnostician 118 or both. In one aspect, these steps may be executed before the decision is made as to whether or not further analysis is required.

Figure 4:
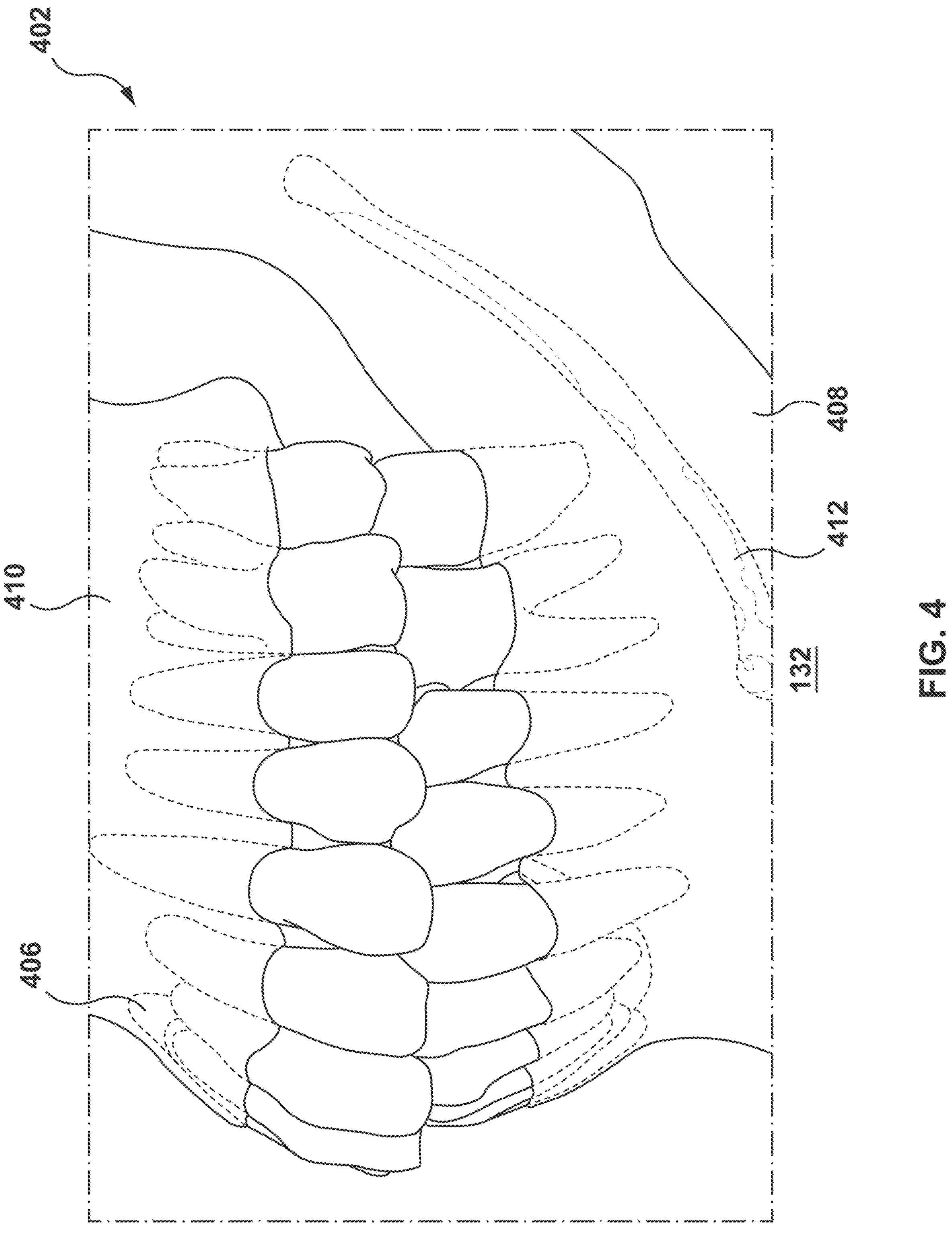
FIG. 4 illustrates an image set, according to one aspect.

FIG. 4 illustrates an image set 132 having a diagnosis region 402 according to one aspect. In the aspect of FIG. 4, image set 132 is an image volume generated following an x-ray scanning operation of a portion of a patient's head, particularly their dentition. It should be understood that image set 132 may include as few as a single image or many images, such as in an image series. The volumetric image of FIG. 4 is generated by a large number of individual x-ray images known as "slices" which are assembled to generate the volumetric image shown in FIG. 4. The image set 132 may take other forms depending on the diagnostic needs.

Diagnosis region 402 includes representations of teeth 406, a representation of mandible 408, representation of maxilla 410 and representation of mandibular canal 412 and representations of some surrounding soft tissues.

In the aspect of FIG. 4, the representations of teeth 406 have been segmented and labeled so that representations of individual teeth are isolated from one another and from the surrounding representation of mandible 408 and representation of maxilla 410. Segmentation may be performed by any suitable software, such as but not limited to diagnostic software 120 having segmentation module 228. Although the representation of tooth 406 are segmented in the aspect shown in FIG. 4, it is not required at this stage for execution of the functions or method steps defined herein.

In FIG. 5, diagnosis region 402 is shown having a region of interest 404 surrounded by a bounding box in the form of a three-dimensional, cuboid 502. The region of interest includes a representation of one tooth 406. However, the bounding box 502 also surrounds a portion of representation of maxilla 410 and portions of other representations of teeth 406. Accordingly, in the aspect shown in FIG. 5, the contours of the bounding box do not exactly match the contours of the region of interest 404. It should be understood that the representation of the oral structures shown in FIG. 4 is limited to the representation of tooth 406 and representation of maxilla 410 for illustrative purposes only. In other aspects, the oral structures represented in the image data may include representations of other teeth, other portions of the jawbones and other oral structures including both soft and hard tissues. Moreover, the bounding box may be three-dimensional or two-dimensional depending on whether the image set is three-dimensional or two-dimensional, respectively. The bounding box may be added by the first diagnostician 118 or by an automated system using a suitable tool or utility within diagnostic software 120. Such a tool or utility might be included as a component of the assignment module 202, the annotation module 210 or the image processing module 226, for example. The bounding box is coupled in data exchange communication with the annotation module 210 so that annotations may be created, edited or removed in association with the data within the bounding box in accordance with one or more of the aspects described herein.

Figure 6:
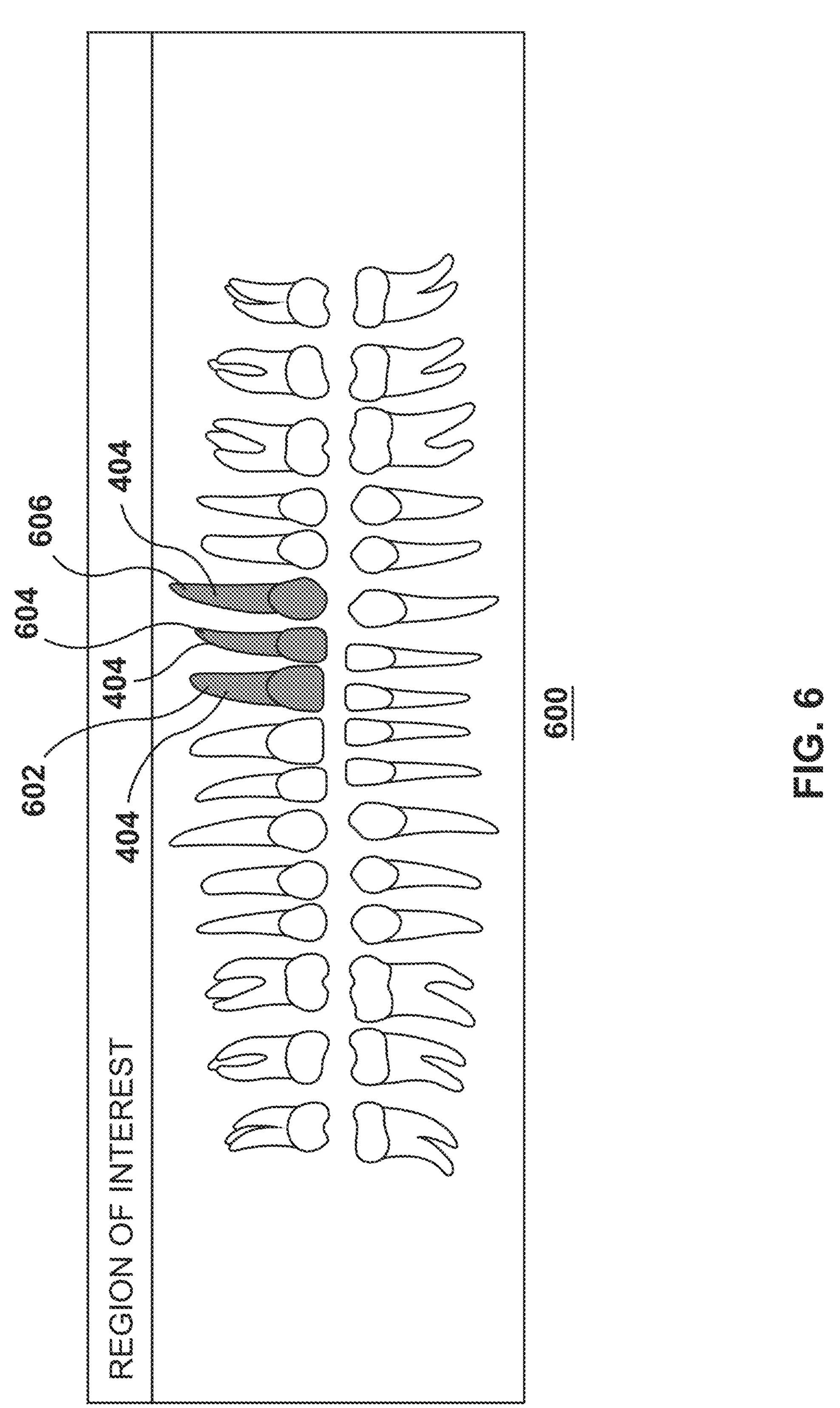
FIG. 6 illustrates a region of interest, visualized according to one aspect.

The drawing of a bounding box about the region of interest is not the only means by which the region of interest may be defined. In FIG. 6, there is shown a graphical user interface 600 to which the segmented teeth of the image set 132 shown in FIG. 4 are mapped. In using graphical user interface 600, a user may select individual teeth to be identified as the region of interest 404. In the example shown in FIG. 6, a central incisor 602, lateral incisor 604 and cuspid 606 are highlighted and are therefore selected to be included in the region of interest 404. This may be reflected in the image set 132 by changing the color of the corresponding tooth representations in the image set 132 or by surrounding the corresponding tooth representations with a suitable bounding box which may be automatically generated by an artificial intelligence module 230 embedded or in communication with diagnostic software 120. Preferably, the teeth identified as components of region of interest 404 are linked to representations of teeth 406 in image set 132 so that a user interacting with graphical user interface 600 may select one or more of the teeth within graphical user interface 600 to then be directed to the volumetric visualization of image set 132 so that they may inspect and analyze the patient imaging data directly.

Figure 7:
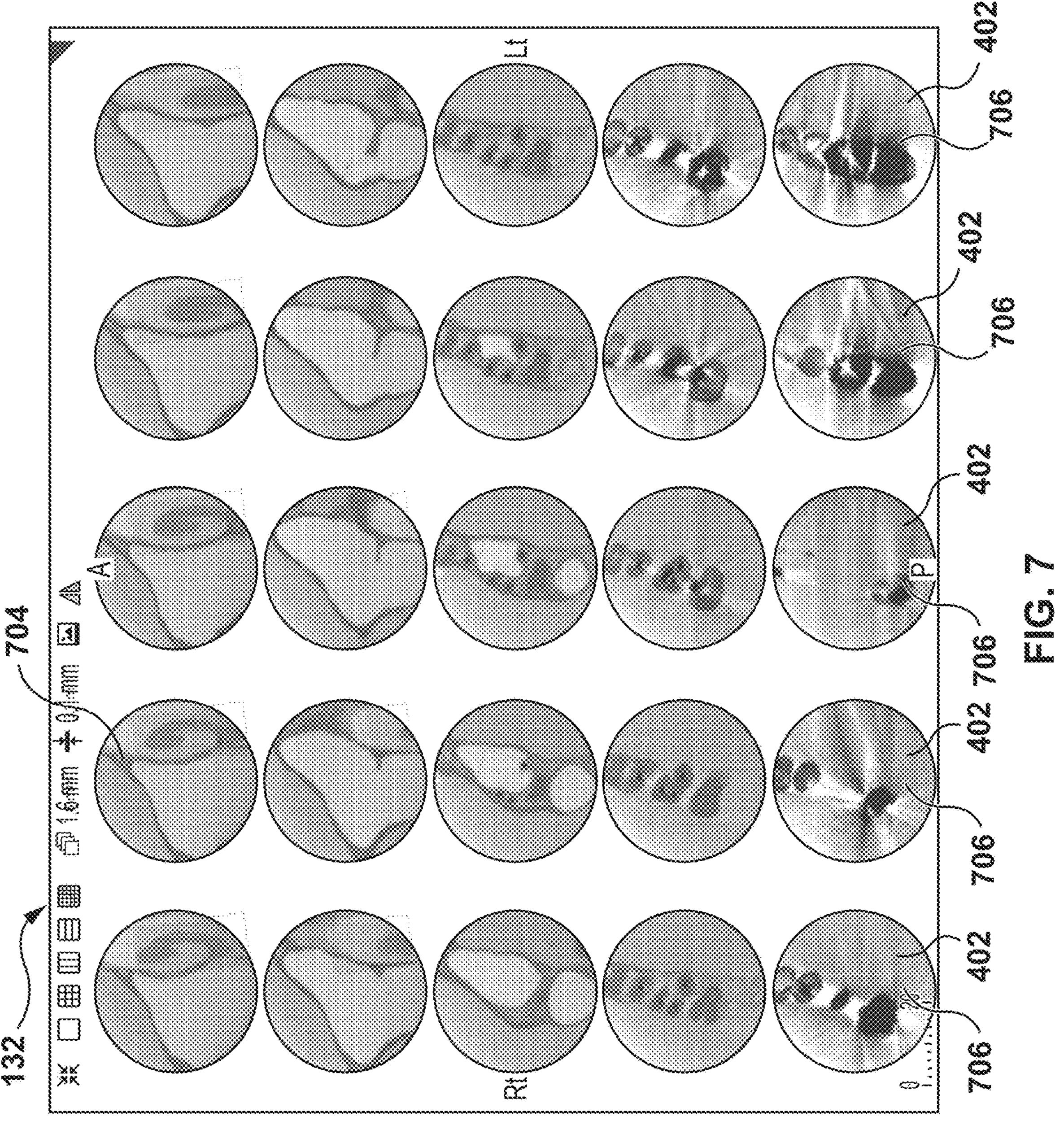
FIG. 7 illustrates an image set, visualized according to one aspect.

FIG. 7 illustrates another means by which the diagnosis region 402 may be defined using a series of individual images 706, according to another aspect. The individual images 706 may be “slices” or section view of an image set 132 consisting of a volumetric image, for example. This visualization allows for first diagnostician 118 to view the diagnosis region 402 from multiple perspectives in a single view.

In one aspect, the scope of diagnosis region 402 within each image 706 of the image series 704 may be communicated to the first diagnostician 118 such as by way of a visually apparent boundary around the diagnosis region 402, a defined set of coordinates and, in one aspect, by highlighting the diagnosis region 402 in a color range while leaving the remainder of the image data in greyscale or a different color range.

In the aspect shown in FIG. 7, diagnosis region 402 encompasses the entirety of each image 706. In this example, the first diagnostician 118 is responsible for reviewing and interpreting all of the data in the entire image series 704 because the first diagnostician 118 is professionally liable for interpreting all of the information available in the entire image set 132.

Figure 8:
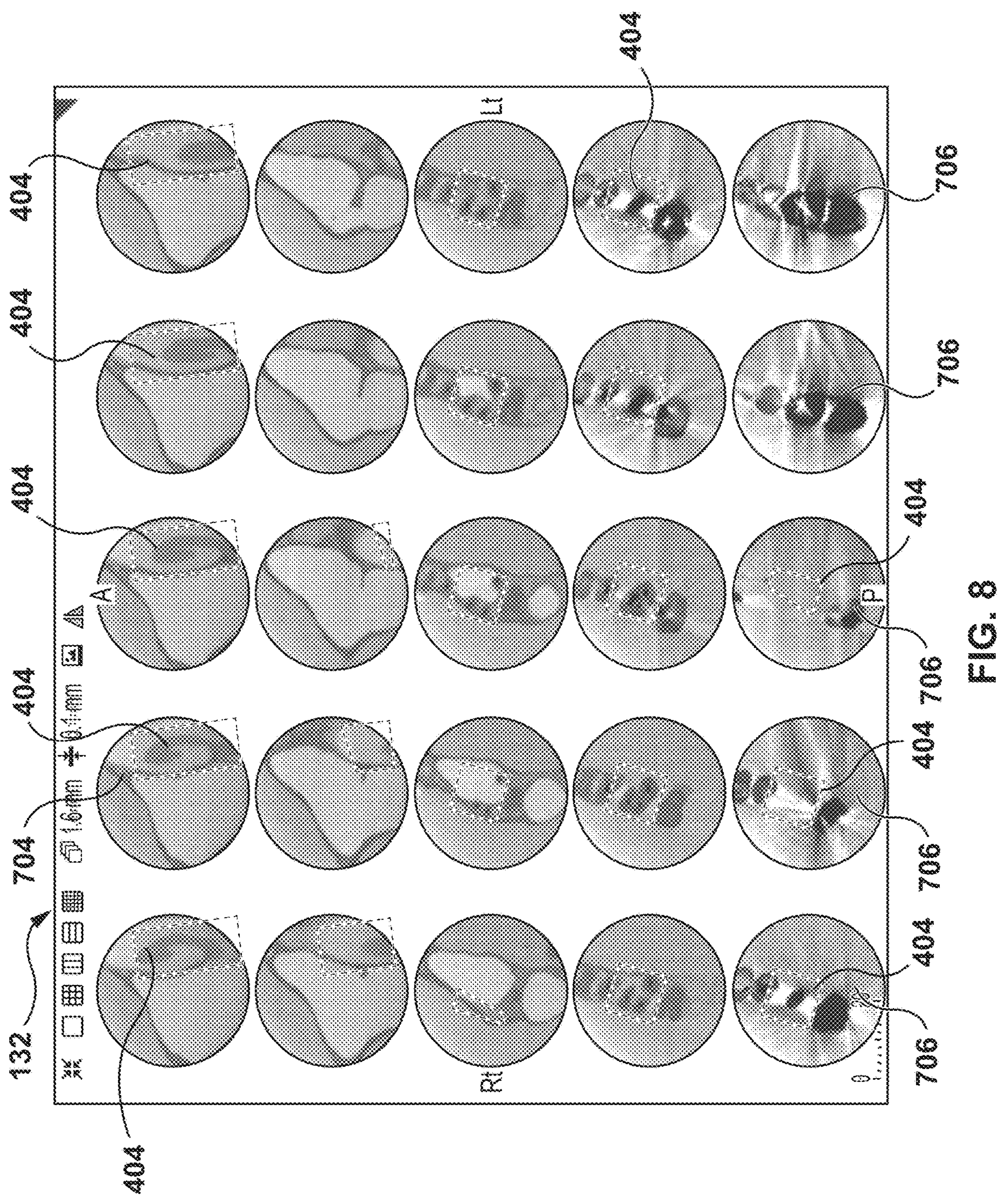
FIG. 8 illustrates an image set, visualized according to one aspect.

FIG. 8 shows the image set 132 of FIG. 7 with a region of interest 404 defined for review by the second diagnostician 126. Region of interest 404 may be defined within the volumetric image set 132. Where the visualization of the image set 132 is presented as an image series 704 consisting of section views of the image set 132, the region of interest 404 appears as a rectangular subsection of the diagnosis region 402 in images 706 of the image series 704.

Region of interest 404 may be highlighted in any suitable manner, including those previously described for identification of the diagnosis region 402. In one aspect, region of interest 404 may be defined using a distinguishable first color range, to make the region of interest 404 visually apparent to the second diagnostician 126. This is as opposed to the remainder of the image data being in a second color range, such as greyscale, which makes the image data that is not the responsibility of second diagnostician 126 less apparent.

Although the aspect illustrated in FIG. 8 is within the context of a first diagnostician 118 assigning to a second diagnostician 126, it should be understood that further regions may be identified for review by a supplementary diagnostician, such as a third diagnostician or a fourth diagnostician, etc., whose findings may be reported back to any of the previous diagnosticians and preferably the first diagnostician 118.

All parties involved with diagnosis of the information presented in the image set 132 can clearly identify and visualize the regions for which they are responsible. For example, the second diagnostician 126 is not responsible or accountable for any region of the image set 132 which is outside of the region of interest 404. The first diagnostician 118 retains responsibility for all regions of the image set 132. If permissions allow, previous diagnosticians in the chain of responsibility may also view regions of the image set 132 which were referred by them to a subsequent diagnostician. This visibility may be cumulative back to the first diagnostician 118 who made the initial referral to the second diagnostician 126.

This partitioning of responsibility using identifiable regions in the image set 132 reduces the time and effort required by the second diagnostician 126 and/or subsequent diagnosticians. The diagnosis by second diagnostician 126 is limited to the regions of interest 404, and typically answers a specific question or series of questions, as further described herein. However, there is no need for the second diagnostician 126, or any subsequent diagnosticians, to exert the time or effort required to assess the entire image series 704.

The aspects shown in FIG. 7 and FIG. 8 illustrate the diagnosis region 402 and region of interest 404, respectively, as they would appear in a two-dimensional visualization. In other aspects, first diagnostician 118 and/or second diagnostician 126 may review image set 132 in or alongside its three-dimensional volumetric visualization, such as that acquired from a CT scanning operation.

Figure 9:
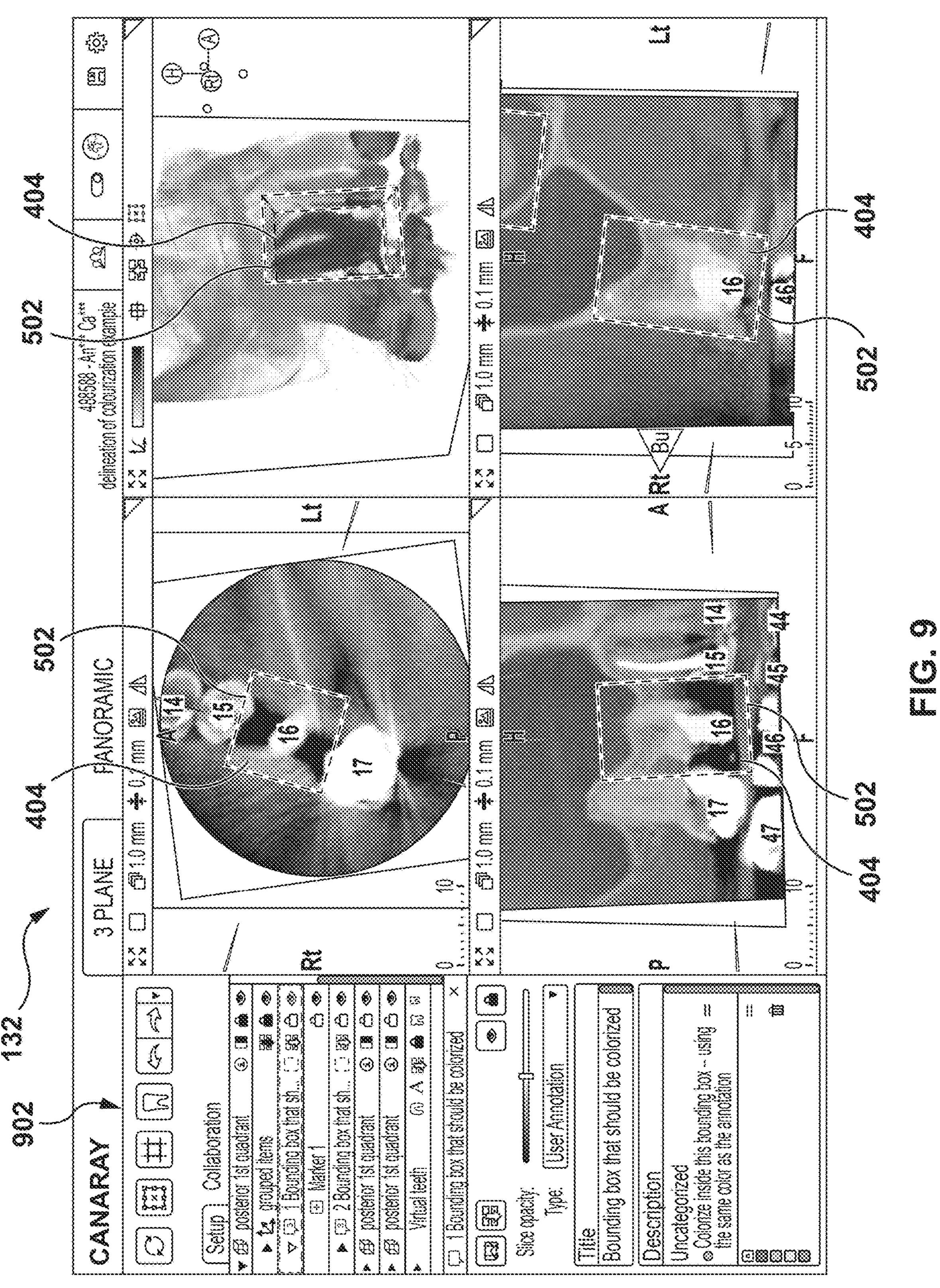
FIG. 9 illustrates an image set, visualized according to one aspect.

FIG. 9 illustrates a region of interest 404 visualized within a three-dimensional environment. The region of interest 404 of the image set 132 to be reviewed in the aspect of FIG. 9 is outlined by way of a three-dimensional bounding box 502. The perspective view of the image set 132 and bounding box 502 may be adjusted by the first diagnostician 118 or second diagnostician 126 as needed, using appropriate interface tools 902.

In the example shown in FIG. 9, a cuboid subsection of voxel data is assigned to the second diagnostician 126 and is identified by voxels having a first color range, such as those identifiable by a green hue, as opposed to the voxels that remain in a second color range, such as greyscale, which are not the responsibility of the second diagnostician 126 that has been assigned the region of interest 404.

Reduction in the region of review for the second diagnostician 126 to the region of interest 404 is advantageous in that it reduces diagnostic review time by the second diagnostician 126, it reduces the turnaround time in providing the second diagnostician 126 report to the first diagnostician 118, it reduces cost by limiting review of the second diagnostician 126 to particular regions of the image set 132, and it reduces duplication of effort by various diagnosticians. Moreover, this method enables the obtaining of highly specialized assessments of specific zones of anatomy inside an image volume or image series or image by a variety of experts, rather than relying on a single expert to assess an entire image or series of images.

In one aspect, the information delineating the region of interest 404 to be reviewed by the second diagnostician 126 is platform-agnostic and so can be viewed on any compatible software platform or system. Therefore, a third-party service provider of image analysis may implement a system that will allow them to request and/or assess subsections of an image series in a way that is compatible with the system that first diagnostician 118 is already using for manual self-diagnosis or automated diagnostic tasks. The region of delineation of responsibility shown in the first color range, such as green can be systematically transferred between systems, permitting users to continue to any compatible system and to communicate with each other transparently, using this definitive method of delineating and identifying regions of interest.

Figure 10:
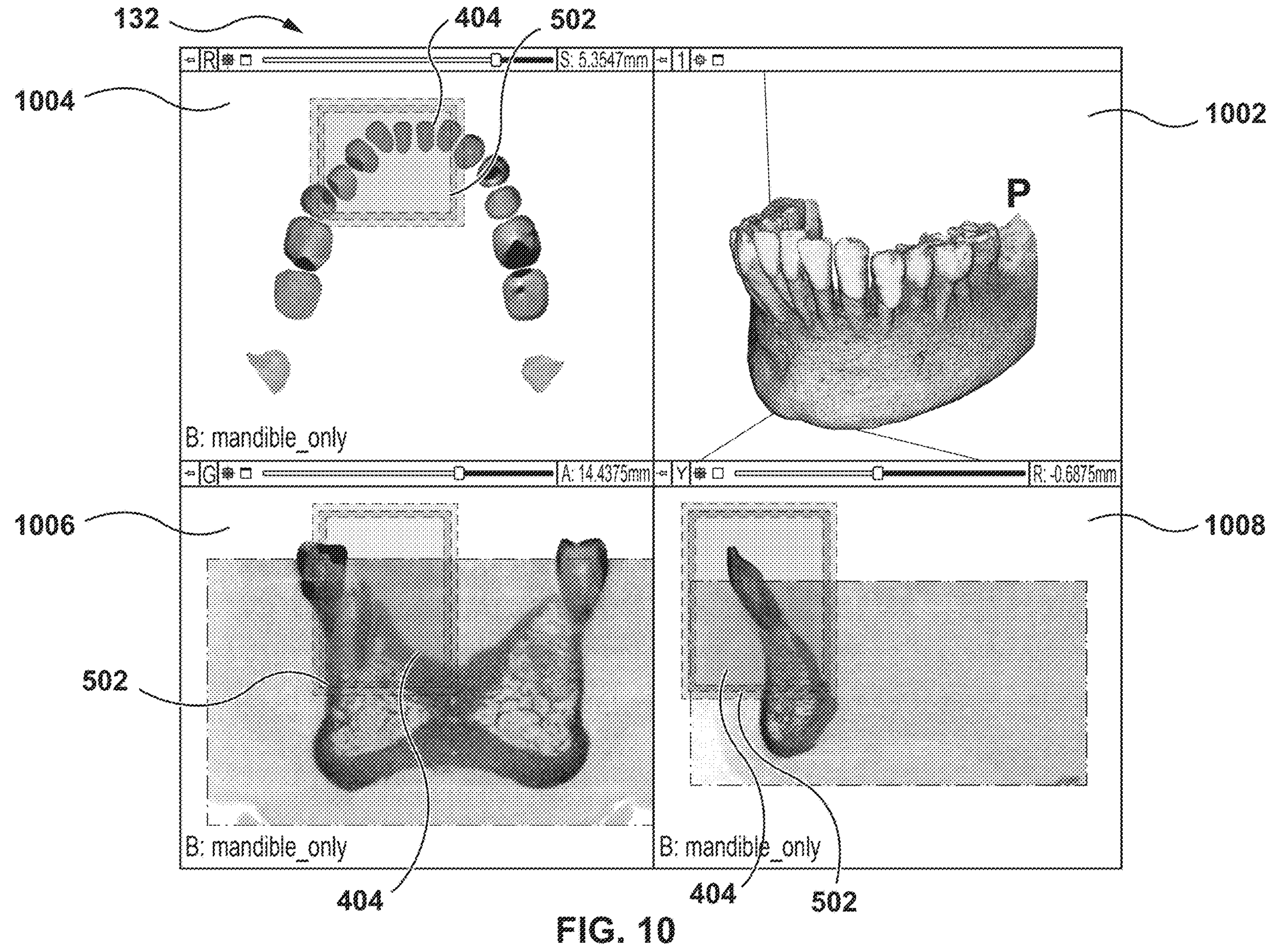
FIG. 10 illustrates an image set, visualized according to one aspect.

FIG. 10 illustrates a region of interest 404 as visualized according to another aspect wherein three-dimensional volumetric views of the image set 132 and two-dimensional section views of the image set 132 are displayed together.

In FIG. 10, the volumetric patient data is shown in a first quadrant 1002. The orientation of the volumetric patient data may be manipulated within first quadrant 1002 so that the volumetric patient data may be viewed from different perspectives. Two-dimensional perspectives of the patient data are shown in second quadrant 1004, third quadrant 1006 and fourth quadrant 1008 according to various predetermined perspectives. The predetermined perspectives may be any desired perspective and may be changed as needed by selection from a user, such as by using tools 902. In the aspect shown in FIG. 10, second quadrant 1004 illustrates the patient data in a top-down perspective, third quadrant 1006 provides a view of the patient data along a first section of the region of interest 404 and fourth quadrant 1008 provides a view of the patient data along a second section of the region of interest 404 perpendicular relative to the first section of the region of interest 404.

Therefore, by way of the aspect shown in FIG. 10, patient data may be viewed according to several perspectives simultaneously and the volumetric patient data may be manipulated to change the information seen in each perspective view.

Figure 11:
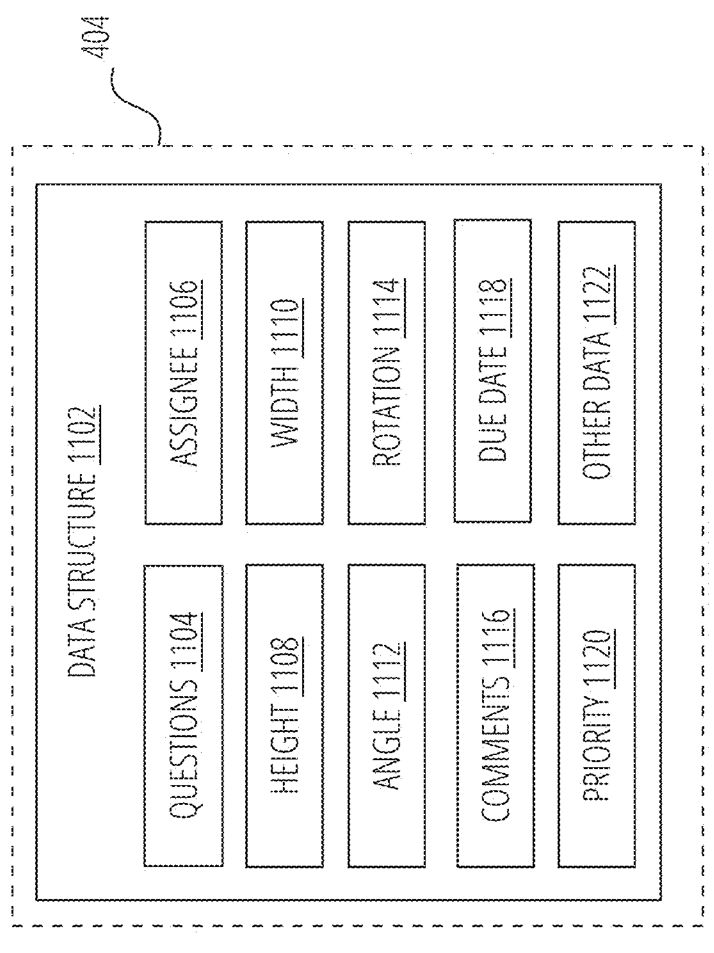
FIG. 11 illustrates a data structure, according to one aspect.

Once the region of interest 404 has been defined, it has associated therewith a data structure 1102 containing data points, as shown in FIG. 11. The region of interest 404 along with the associated data structure 1102 is transmitted by suitable means from the first diagnostician 118 to a compatible service of the second diagnostician 126 for review of the information contained within the region of interest 404.

Data structure 1102 includes any relevant data points associated with the region of interest 404 and which may be relevant to the first diagnostician 118 or the second diagnostician 126. This may include, for example, the height 1108, width 1110, angle 1112, rotation 1114 of the region of interest 404 or structures therewithin, or other data points which may be relevant to review and interpretation of the region of interest 404. Data structure 1102 also includes the assignee 1106, who is the second diagnostician 126 to which review is assigned, identified by way of a contact name, email address, serial number or other information. Data structure 1102 further includes a field containing questions, annotations or notes from the first diagnostician and may also include a priority level 1120 and due date 1118. This information acts as a frame of reference for the second diagnostician 126. For example, the first diagnostician 118 may have a specific question to be answered by the second diagnostician 126 related to the region contained within the bounding box 502. Data structure 1102 may further include a field for comments 1116 which the second diagnostician 126 may populate with their own notes, comments and annotations to be directed back to the first diagnostician 118 once review is complete.

It should be understood that, in a preferred aspect, the second diagnostician 126 is not presented with an option to comment on areas outside of the region of interest 404. Accordingly, comments 1116 are limited to the region of interest 404 within the bounding box 502.

Once review by the second diagnostician 126 has been completed, a report on the analyzed region of interest 404 is created and sent to the first diagnostician 118. The report includes any second diagnostician annotations, such as data entered into the data structure 1102. The report may be sent via network 124, for example. Upon the eventual receipt of the diagnostic result by the first diagnostician 118, the first diagnostician 118 may then synthesize data from their own analysis and from the second diagnostician 126 to obtain a final diagnostic outcome for the image set 132.

In a preferred aspect, there is no option for the data structure 1102 to be altered once it has been transmitted from the first diagnostician 118 to the second diagnostician 126 or vice versa. Accordingly, the integrity of the data structure 1102 associated with the region of interest 404 is maintained throughout the chain of interaction between the first diagnostician 118 and the second diagnostician 126 or other diagnosticians to which the case may be referred.

Figure 12:
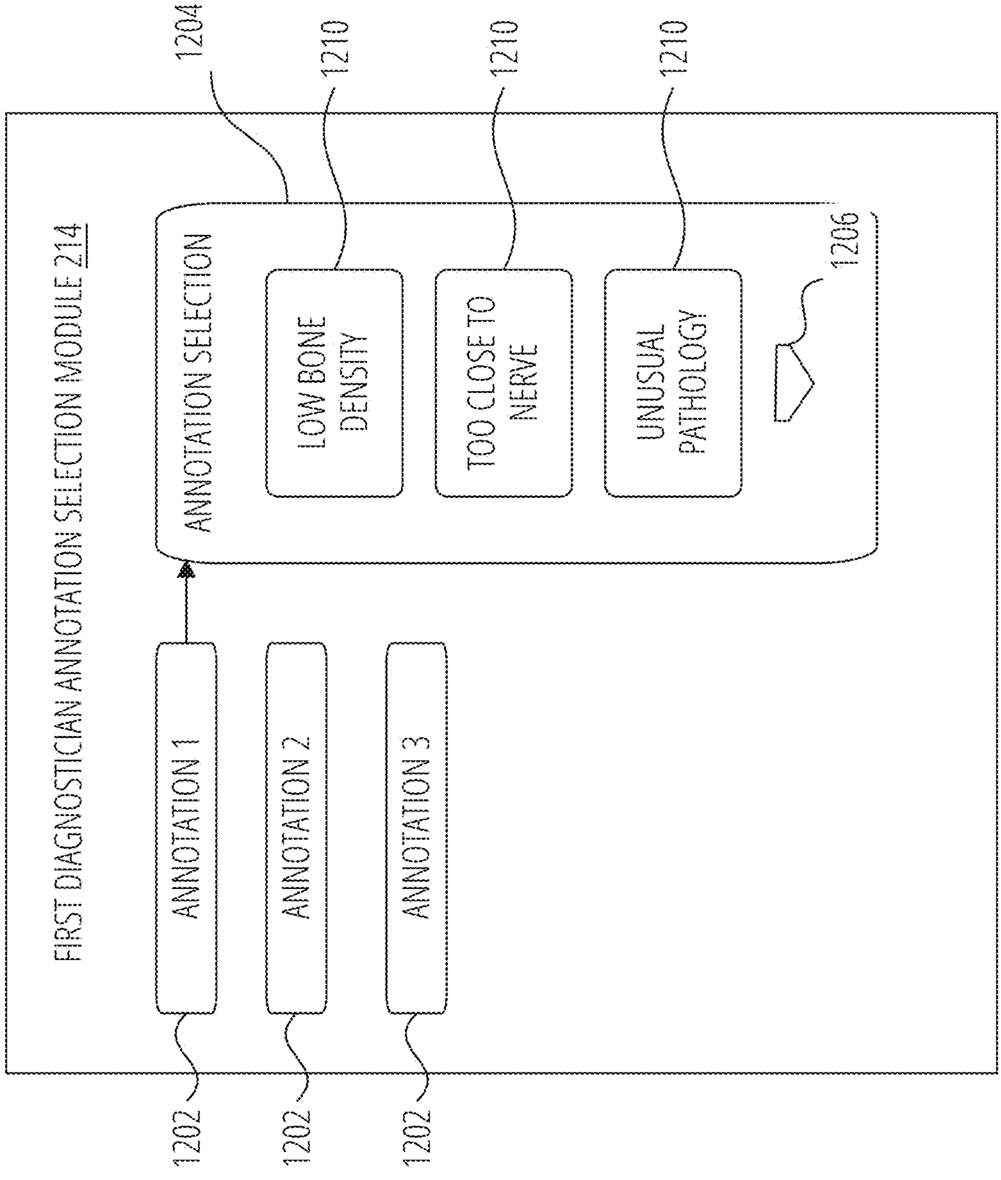
FIG. 12 illustrates a module, according to one aspect.

In FIG. 12, there is shown first diagnostician annotation selection module 214 for first diagnostician 118 to make at least one first diagnostician annotation 1302 (FIG. 13), for application to the region of interest 404, according to one aspect. In this aspect, the first diagnostician 118 may select one of a plurality of annotation fields 1202. Upon selection of an annotation field 1202, first diagnostician 118 is presented with a predetermined list of available template annotations 1210, one of which may be input to the associated annotation field 1202. This presentation may be made, for example, using a dropdown menu 1204 or other suitable control.

Figure 13:
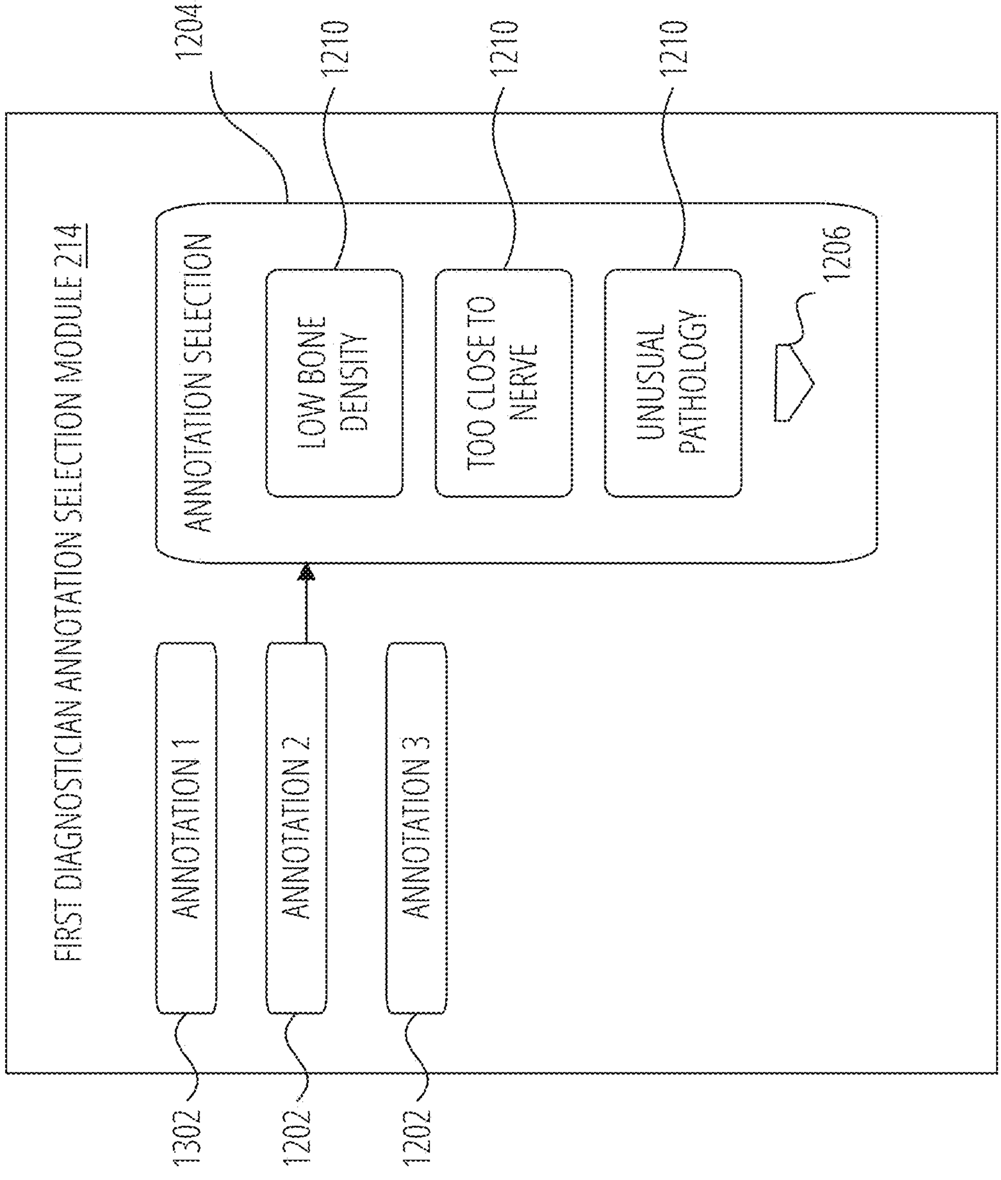
FIG. 13 illustrates the module of FIG. 12, according to one aspect.

First diagnostician 118 may select the desired template annotation 1210 from dropdown menu 1204 which is then input to the associated annotation field 1202 to create first diagnostician annotation 1302 as shown in FIG. 13.

If the desired template annotation 1210 is not visible among the displayed options in dropdown menu 1204, first diagnostician 118 may scroll to view additional options using, for example, scroll button 1206. In another aspect, a customizable template annotation 1210 is available for first diagnostician 118 to input custom remarks.

Standardization of the annotations prevents miscommunication and lack of clarity between first diagnostician 118 and second diagnostician 126 to whom the annotations are directed. Thereby, turnaround time is reduced and the patient can expect a clearer result. It should be understood that although FIG. 12 illustrates only three fields for first diagnostician annotation 1302, it should be understood that any number of first diagnostician annotations 1302 may be presented to second diagnostician 126 for analysis.

In another aspect, the annotation system may simply include one or more fields within which text, image, audio or video information may be entered by the first diagnostician 118. In this aspect, the system for entering information provides flexibility in how the information may be entered.

Figure 14:
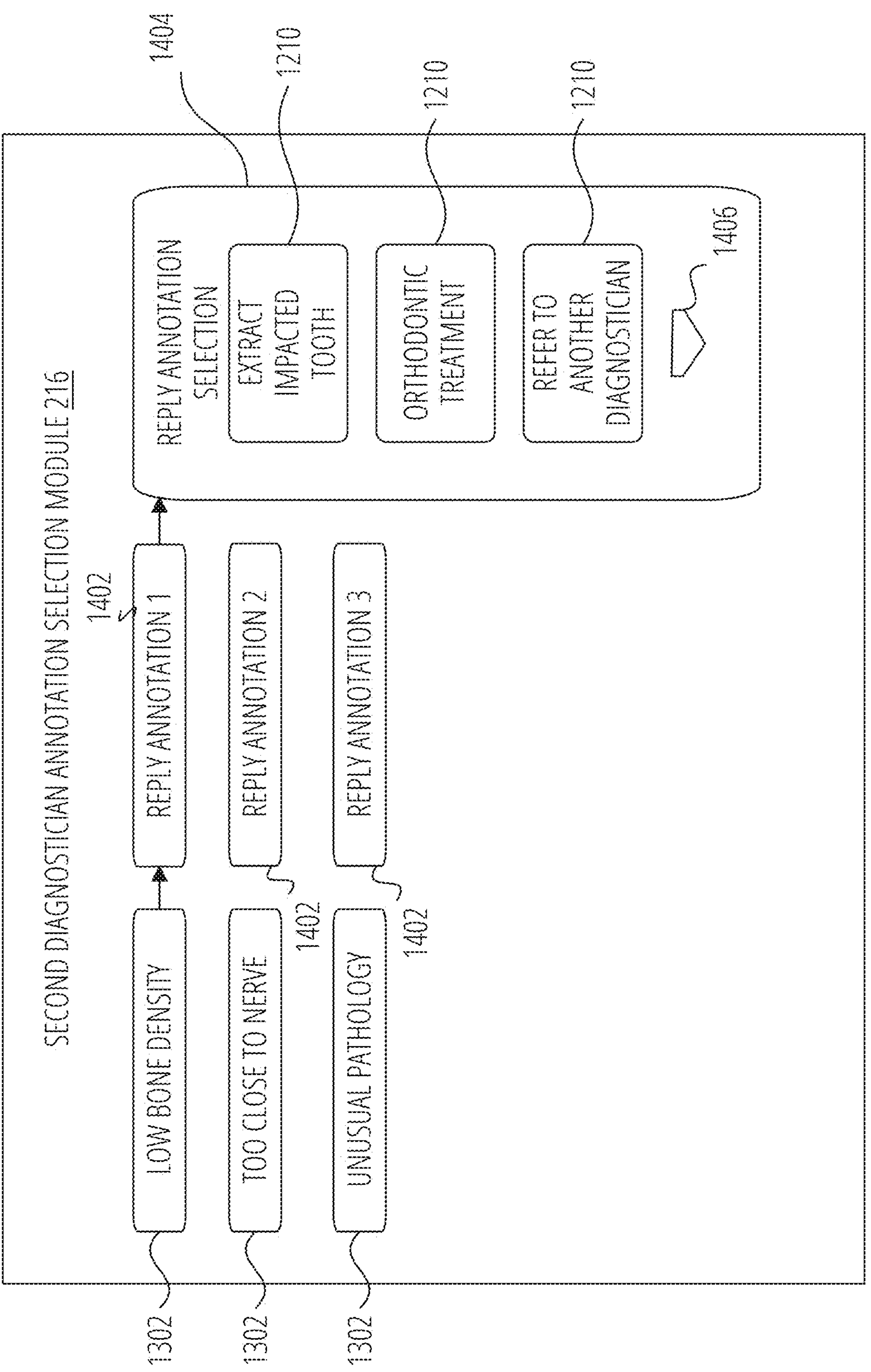
FIG. 14 illustrates a module, according to one aspect.

In FIG. 14, there is shown second diagnostician annotation selection module 216 for second diagnostician 126 to make at least one second diagnostician annotation 1502 (FIG. 15) within region of interest 404, according to one aspect. In this aspect, second diagnostician 126 is presented with first diagnostician annotations 1302 to be analyzed and a plurality of reply annotation fields 1402. Upon selection of a reply annotation field 1402, second diagnostician 126 is presented with a predetermined list of available template annotations 1210, one of which may be input to the associated reply annotation field 1402. This presentation may be made, for example, using a dropdown menu 1404 or other suitable control.

Figure 15:
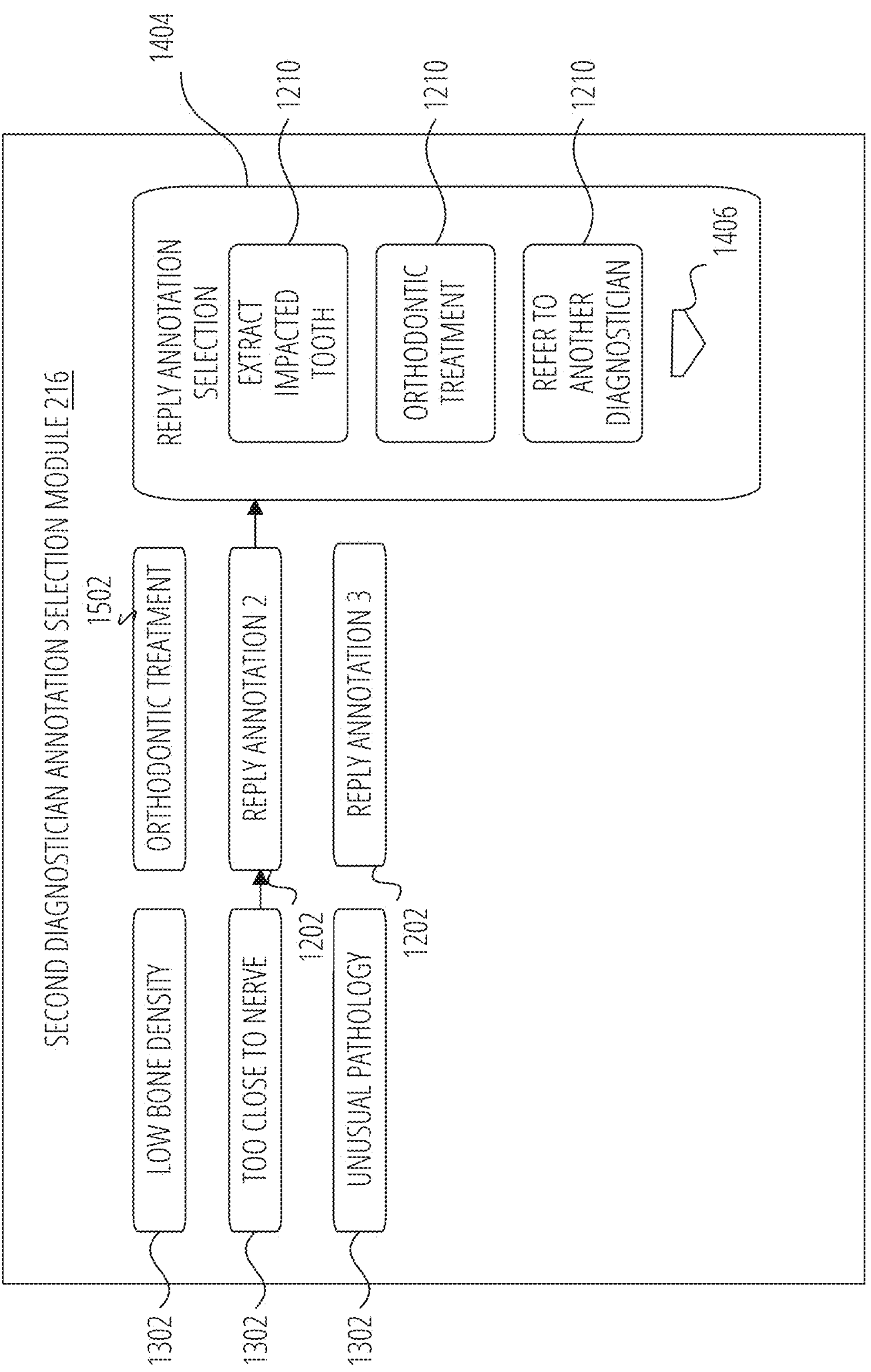
FIG. 15 illustrates the module of FIG. 14, according to one aspect.

Second diagnostician 126 may select the desired template annotation 1210 from dropdown menu 1404 which is then input to the associated reply annotation field 1402 to create second diagnostician annotation 1502 as shown in FIG. 15.

If the desired annotation is not available among the displayed options in dropdown menu 1404, second diagnostician 126 may scroll to view additional options using, for example scroll button 1406. In another aspect, a customizable template annotation 1210 is available for second diagnostician 126 to input custom remarks.

It should be understood that the list of available template annotations 1210 presented in dropdown menu 1404 depends on the value in the corresponding first diagnostician annotation 1302 and that the available template annotations 1210 made available to second diagnostician 126 may change from one first diagnostician annotation 1302 to another. For example, if first diagnostician 118 provided as an annotation "Low Bone Density" as shown in FIG. 12, second diagnostician 126 would be presented with a first list of template annotations 1210 from which reply may be selected. However, if first diagnostician 118 provided as an annotation "Too Close to Nerve", as shown in FIG. 12, second diagnostician 126 would be presented with a second list of template annotations 1210 from which reply may be selected, which may include at least some different responses from those presented as options in the first list of template annotations 1210. Accordingly, the list of available reply options for selection may change partially or completely depending on any of the other first diagnostician annotation 1302 selected by first diagnostician 118. Standardization of the reply annotations prevents miscommunication and lack of clarity between second diagnostician 126 and first diagnostician 118 to whom the reply annotations are directed. Thereby, turnaround time is reduced and the patient can expect a clearer result.

In another aspect, the annotation system may simply include one or more fields within which text, image, audio or video information may be entered by the second diagnostician 126. In this aspect, the system for entering information provides flexibility in how the information may be entered.

While the invention has been described in terms of specific aspects, it is apparent that other forms could be adopted by one skilled in the art. For example, the methods described herein could be performed in a manner which differs from the aspects described herein. The steps of each method could be performed using similar steps or steps producing the same result but which are not necessarily equivalent to the steps described herein. Some steps may also be performed in different order to obtain the same result. Similarly, the apparatuses and systems described herein could differ in appearance and construction from the aspects described herein, the functions of each component of the apparatus could be performed by components of different construction but capable of a similar though not necessarily equivalent function, and appropriate materials could be substituted for those noted. Accordingly, it should be understood that the invention is not limited to the specific aspects described herein. It should also be understood that the phraseology and terminology employed above are for the purpose of disclosing the illustrated aspects, and do not necessarily serve as limitations to the scope of the invention.

What is claimed is:

1. A computer-implemented method performed by one or more processors executing instructions stored on a non-transitory computer-readable medium, the method comprising:

acquiring an image set including at least one image;

assigning a diagnosis region within the image set to a first diagnostician for analysis;

defining a region of interest within the diagnosis region and generating a data structure associated with the region of interest, the data structure including (i) geometric parameters defining the region of interest, (ii) an assignee identifier, and (iii) at least one first diagnostician annotation field;

defining, via the first diagnostician, at least one first diagnostician annotation within the region of interest and storing the at least one first diagnostician annotation in the first diagnostician annotation field of the data structure;

assigning the region of interest and the at least one first diagnostician annotation to a second diagnostician for analysis by transmitting the data structure to a computer system accessible to the second diagnostician;

preventing post-transmission alteration of the geometric parameters, the assignee identifier, and the first diagnostician annotation stored in the data structure to maintain integrity of the data structure throughout a chain of interaction between the first diagnostician and the second diagnostician;

granting the second diagnostician view-only permission for image data of the diagnosis region located outside of the region of interest to prevent the second diagnostician from defining annotations outside of the region of interest while the image data outside of the region of interest remains viewable by the second diagnostician;

defining, via the second diagnostician, at least one second diagnostician annotation within the region of interest; and, reporting the analyzed region of interest having the at least one second diagnostician annotation to the first diagnostician.

2. The method of claim 1, further comprising:

determining whether further analysis is required, and if further analysis is required, then, defining at least one additional first diagnostician annotation within the region of interest and storing the additional first diagnostician annotation in a further field of the data structure without altering the first diagnostician annotation, the assignee identifier, or the geometric parameters previously stored in the data structure;

assigning the region of interest with the at least one additional first diagnostician annotation to the second diagnostician for review; and, defining, via the second diagnostician, at least one additional second diagnostician annotation within the region of interest.

3. The method of claim 1, wherein the at least one first diagnostician annotation is selected by the first diagnostician from a first predetermined list of template annotations.

4. The method of claim 3, wherein the at least one second diagnostician annotation is selected by the second diagnostician from a second predetermined list of template annotations, wherein the content of the second predetermined list of template annotations is determined by the specific template annotation selected by the first diagnostician as the at least one first diagnostician annotation, such that a first template annotation selected by the first diagnostician yields a different second predetermined list than a second template annotation selected by the first diagnostician.

5. The method of claim 1, wherein the image set includes a three-dimensional volumetric image.

6. The method of claim 5, wherein defining the region of interest of the image set to be reviewed includes:

outlining, within a bounding box, a three-dimensional region of the volumetric image having the region of interest therein.

7. The method of claim 1, wherein the region of interest is a component of a collaborative digital infrastructure accessible by both the first diagnostician and the second diagnostician and assigning the region of interest to the second diagnostician for review is done within the collaborative digital infrastructure.

8. The method of claim 1, further comprising:

assigning a sub-region of the region of interest to at least one supplementary diagnostician for analysis;

wherein the first diagnostician and the second diagnostician retain view access to the sub-region and to annotations entered by the supplementary diagnostician within the sub-region.

9. The method of claim 8, wherein assigning the sub-region is by one of the first diagnostician and the second diagnostician.

10. The method of claim 8, further comprising:

reporting the analyzed sub-region to at least one of the first diagnostician and the second diagnostician.

11. A system comprising: one or more processors and a non-transitory computer-readable memory storing instructions that, when executed by the one or more processors, cause the system to:

acquire an image set including at least one image;

assign a diagnosis region within the image set to a first diagnostician for analysis;

define a region of interest within the diagnosis region and generate a data structure associated with the region of interest, the data structure including (i) geometric parameters defining the region of interest, (ii) an assignee identifier, and (iii) at least one first diagnostician annotation field;

define, via the first diagnostician, at least one first diagnostician annotation within the region of interest and store the at least one first diagnostician annotation in the first diagnostician annotation field of the data structure;

assign the region of interest and the at least one first diagnostician annotation to a second diagnostician for analysis by transmitting the data structure to a computer system accessible to the second diagnostician;

prevent post-transmission alteration of the geometric parameters, the assignee identifier, and the first diagnostician annotation stored in the data structure, to maintain integrity of the data structure throughout a chain of interaction between the first diagnostician and the second diagnostician;

grant the second diagnostician view-only permission for image data of the diagnosis region located outside of the region of interest to prevent the second diagnostician from defining annotations outside of the region of interest while the image data outside of the region of interest remains viewable by the second diagnostician;

define, via the second diagnostician, at least one second diagnostician annotation within the region of interest; and, report the analyzed region of interest having the at least one second diagnostician annotation to the first diagnostician.

12. The system of claim 11, wherein the instructions, when executed by the one or more processors, further cause the system to determine whether further analysis is required, and if further analysis is required, then to define at least one additional first diagnostician annotation within the region of interest and store the additional first diagnostician annotation in a further field of the data structure without altering the first diagnostician annotation, the assignee identifier, or the geometric parameters previously stored in the data structure, assign the region of interest with the at least one additional first diagnostician annotation to the second diagnostician for analysis, define, via the second diagnostician, at least one additional second diagnostician annotation within the region of interest, and report the analyzed region of interest having the at least one additional second diagnostician annotation within the region of interest to the first diagnostician.

13. The system of claim 11, wherein the at least one first diagnostician annotation is selected by the first diagnostician from a first predetermined list of template annotations.

14. The system of claim 13, wherein the at least one second diagnostician annotation is selected by the second diagnostician from a second predetermined list of template annotations, wherein the content of the second predetermined list is determined by the specific template annotation selected by the first diagnostician as the at least one first diagnostician annotation, such that a first template annotation selected by the first diagnostician yields a different second predetermined list than a second template annotation selected by the first diagnostician.

15. The system of claim 11, wherein the image set includes a three-dimensional volumetric image.

16. The system of claim 15, wherein the instructions, when executed by the one or more processors, further cause the system to outline, within a bounding box, a three-dimensional region of the volumetric image having the region of interest of the image set to be reviewed therein.

17. The system of claim 11, wherein the region of interest is a component of a collaborative digital infrastructure accessible by both the first diagnostician and the second diagnostician and assigning the region of interest to the second diagnostician for review is done within the collaborative digital infrastructure.

18. The system of claim 11, wherein the instructions, when executed by the one or more processors, further cause the system to assign a sub-region of the region of interest to at least one supplementary diagnostician for analysis; wherein the first diagnostician and the second diagnostician retain view access to the sub-region and to annotations entered by the supplementary diagnostician within the sub-region.

19. The system of claim 18, wherein the instructions, when executed by the one or more processors, further cause the system to report the analyzed sub-region to at least one of the first diagnostician and the second diagnostician.

20. The system of claim 11, wherein at least one of the first diagnostician and the second diagnostician is an automated diagnostician.

* * * * *